(12) United States Patent
Rundell et al.

(10) Patent No.: US 7,341,833 B2
(45) Date of Patent: Mar. 11, 2008

(54) COMPOSITIONS AND METHODS RELATING TO NUCLEIC ACID REFERENCE STANDARDS

(75) Inventors: Clark A. Rundell, Standish, ME (US); Joan Gordon, Old Orchard Beach, ME (US)

(73) Assignee: Maine Molecular Quality Controls, Inc., Scarborough, ME (US)

( * ) Notice: Subject to any disclaimer, the term of this patent is extended or adjusted under 35 U.S.C. 154(b) by 291 days.

(21) Appl. No.: 10/970,954

(22) Filed: Oct. 22, 2004

(65) Prior Publication Data

US 2005/0214792 A1  Sep. 29, 2005

Related U.S. Application Data

(62) Division of application No. 09/866,283, filed on May 25, 2001, now Pat. No. 6,818,762.

(51) Int. Cl.
  *C12Q 1/68* (2006.01)
  *C12P 19/34* (2006.01)
  *C07H 21/02* (2006.01)
  *C07H 21/04* (2006.01)

(52) U.S. Cl. .................... 435/6; 435/91.2; 536/23.1

(58) Field of Classification Search .................... None
  See application file for complete search history.

(56) References Cited

U.S. PATENT DOCUMENTS 4,806,546 A * 2/1989 Carrico et al. ............. 536/25.3

FOREIGN PATENT DOCUMENTS

EP  0 514 513 B1  11/1991
EP  0 819 696 A2  1/1998

OTHER PUBLICATIONS

Hayashid, N. et al., "Construction of a cDNA library for a specific region of a chromosome using a novel cDNA selection method utilizing latex particles", Gene, vol. 165, pp. 155-161 (1995).
Hayatsu, H. et al., "Polynucleotide-Chitosan Complex, an insoluble but Reactive Form of Polynucleotide", Chem. Pharm. Bull., vol. 45, pp. 1363-1366 (1997).
Johnson et al., 2001, J. Biol. Chem. 29:27716-27720.
Kariko, K. et al., "Phosphate-enhanced transfection of cationic lipid-complexed mRNA and plasmid DNA", Biochim. Biphis. Acta, vol. 1369, pp. 320-324 (1998).
Kumar et al., "Detection of Anti-RNA Antibodies in Systemic Lupus Erythematosus by ELISA Using Nylon as Solid Support", Immunology Letters, vol. 7, pp. 293-296 (1984).
Lasic et al., 1997, Liposomes in Gene Delivery, 113-143.
Lee et al., 1996, Human Gene Therapy 7:1701-1717.
Mansfield et al., 1999, BioTechniques 27:1253-1257.
Matsui, M. et al., "Selective Adsorption of Biopolymers on Zeolites", Chemistry Eur, J., vol. 7, pp. 1555-1560 (Apr. 2001).
Matthews, J.A. et al, "Analytical Strategies for Use of DNA Probes", Anal. Biochem., vol. 169, pp. 1-25 (1988).
McConway et al., 1986, J. Immunol. Methods 95: 259-266.
Morales et al., 2000, Biochemistry 39:12979-12988.
Van Germen, B. et al., "One-tune Quantitative HIV-1 RNA NASBA", in PCR Primer: A Laboratory Manual, Cold Spring Harbor Laboratory Press, pp. 667-677 (1995).
Vogelstein et al., 1979, Proc. Natl. Acad. Sci. U.S.A. 76:615-618.
Wurtz et al., 2001, Org. Lett. 8:1201-1203.

* cited by examiner

*Primary Examiner*—Teresa E. Strzelecka
(74) *Attorney, Agent, or Firm*—Drinker Biddle & Reath, LLP

(57) ABSTRACT

The invention relates to novel nucleic acid reference standards comprising a nucleic acid comprising a known target sequence bound with a microparticulate binding agent where the binding agent includes liposomes, polyamines (e.g., nylon), siliceous compounds (e.g., silica gel, fumed silica, diatomaceous earth, glass particles, amine-modified silica, and the like), zeolites (e.g., low alumina zeolyte), polystyrene (e.g., amine-modified polystyrene, carboxy-polystyrene particles, and the like), chitin, chitosan, and combinations of these compounds. The reference standard is useful for use as a standard in any nucleic acid assay where the presence or absence of a nucleic acid of interest is being assessed. The reference standard is stable and provides a control for assessing whether the nucleic acid assay was performed properly. The invention further relates to methods of producing such reference standards and kits for using and producing the same pursuant to the teachings of the invention.

4 Claims, 11 Drawing Sheets

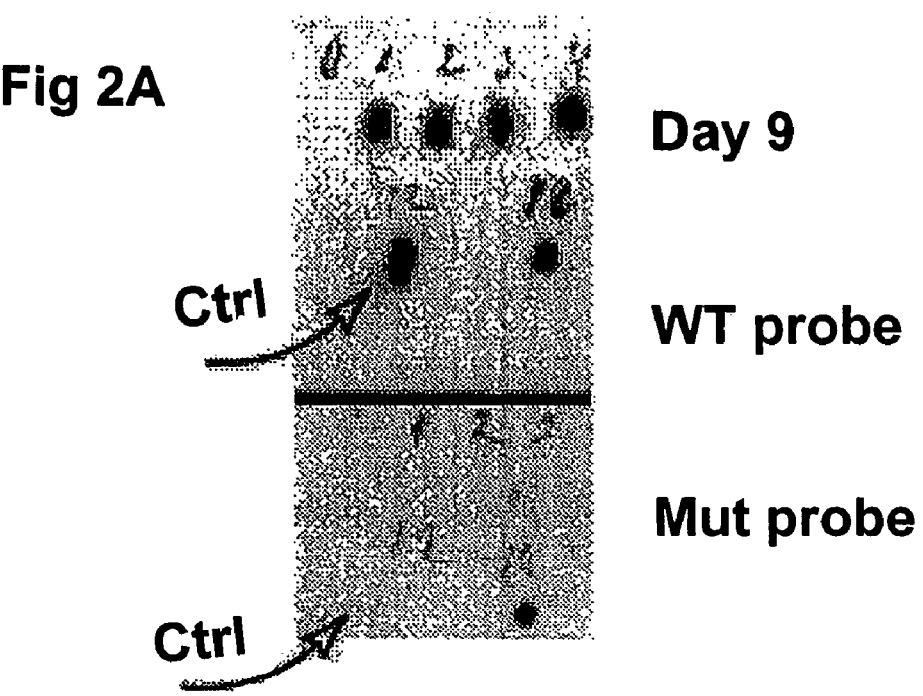
Fig 2A — Day 9, WT probe, Mut probe (Ctrl)
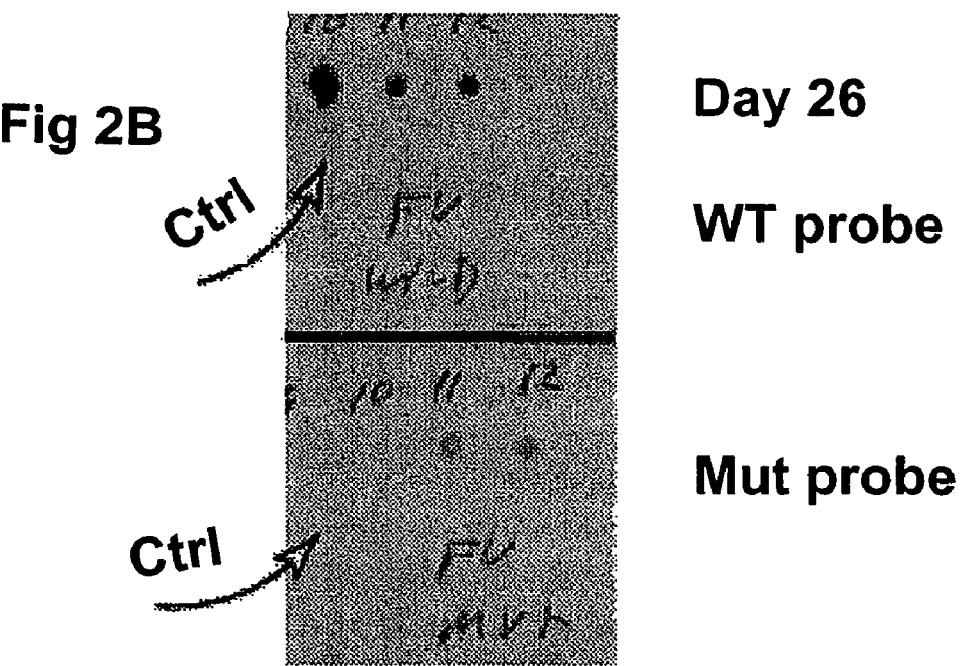
Fig 2B — Day 26, WT probe, Mut probe (Ctrl)
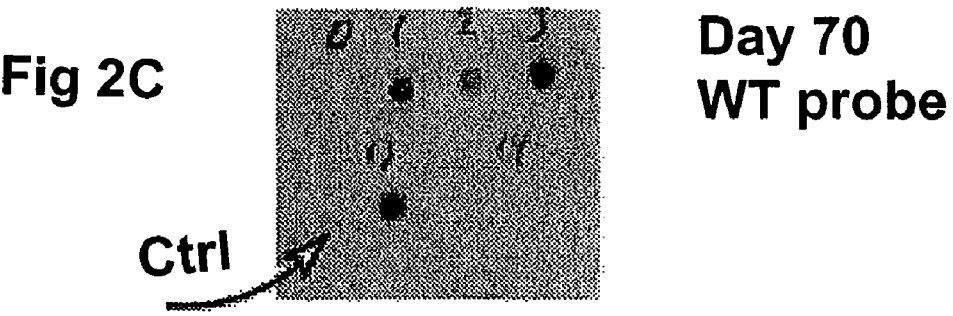
Fig 2C — Day 70 WT probe (Ctrl)

1  2  3  4  5  6  7  8  9  10  11  12  13  14  15

```
62521  AAAGAGCTTTATACTTTTACCAGATGGTATCTCACTGAACCCCCAAACAGACCTGTAACA
62581  TTTTTAGGAGGGTTATTACCCATTTGATAAAGGAAGAAATTAGGAAAGGCTAATCAACT
62641  TGCTCAACACATCCAATACCAACAGACCTGGAATTTGAAACTAAGACAAAATATGTTATC
62701  ACACTCTAGACTTGCCTTCGGCAGTGATGGTACTGATAAAAATAGACAAGACAAAAAAA
62761  AAAAAGAATAAATGTTATCACACTGGTGCTAAAAAGGACTACTTGACAATTACTGTTCTC
62821  TTGAAGGAAATGCCCCATTATTAGCCAGGAGACCTAACATGTTCTAGCCAGAAGAAATT
62881  CTCAGAATTTCTGAAAGGTTACTTCAAGGACAAAATACCTGTATTCCTTGCCTGTCCAGG
62941  GATCTGCTCTTACAGATTAGAAGTAGTCCTGTGTTAAGCACTGGGCATCATTTCTGTGGGTTCATCA
63001  TCCACGTCACTGTAGTATGGTCTTGTTAAGCACTGGGCATCATTTCTGTGGGTTCATCA
63061  AACTCTAAGATGTTCCACTTATAAGAAAATATATTCAAAATGTTTTCATTGCAAAGTTATTTC
63121  GTGTTGTTCCTGCCTGAAAGAAATAATAAGCTTTCGCTGAACCAATTAATATTGCAAAAGGAATTC
63181  ATGATAATAATAAATAAGCTTTCGCTGAACCAATTAATATTGCAAAAGGAATTC
63241  TTTTATTTTTATTTTTTTAAATTATACTTTAAGTTCTAGGGTACATGTGCACAACGTGC
```

FIGURE 9

COMPOSITIONS AND METHODS RELATING TO NUCLEIC ACID REFERENCE STANDARDS

CROSS-REFERENCE TO RELATED APPLICATIONS

This application is a divisional of U.S. patent application Ser. No. 09/866,283, filed May 25, 2001, now U.S. Pat. No. 6,818,762 which is hereby incorporated by reference in its entirety.

STATEMENT REGARDING FEDERALLY SPONSORED RESEARCH OR DEVELOPMENT

This invention was supported in part by funds from the U.S. Government (National Institutes of Health SBIR Grant No. 1 R43 GM62085-01) and the U.S. Government may therefore have certain rights in the invention.

BACKGROUND OF THE INVENTION

Nucleic acids encompass both deoxyribonucleic acid (DNA) and ribonucleic acid (RNA). DNA, present in all nucleated cells, carries the information needed to direct the synthesis of every protein in the body. A single alteration in the correct sequence of the four DNA bases (adenine, thymine, guanine, and cytosine) may result in a defective protein. Depending upon the protein and the affected organism, the defect may range from inconsequential to life-threatening, or may be of intermediate severity. Diseases as diverse as cystic fibrosis, some types of cancer, sickle cell anemia, and atherosclerosis are known to result from specific genetic alterations.

RNA, the intermediary between DNA and protein, is the product of transcription of a DNA template. RNA assays are being performed with increasing frequency in research and clinical laboratories. This is due at least in part to the prevalence of RNA viruses such as the human immunodeficiency virus (HIV) that causes AIDS and the hepatitis C virus (HCV), and the development of drugs used in treating infections with RNA viruses.

Nucleic acid assays are routinely performed, either manually or by automated instrumentation, in numerous reference and clinical laboratories. A nucleic acid assay may be performed to detect the presence of foreign DNA or RNA, which may indicate infection with a foreign organism. For example, a variety of molecular assays are used to establish the presence and identity of nucleic acids from the human immunodeficiency virus-1 (HIV-1), Chlamydia, and other organisms causing sexually transmitted diseases.

An individual's DNA may also be analyzed to detect, treat, and in some cases prevent genetic disease. Genotype determination of genes for factor V Leiden, hereditary hemochromatosis, lipoprotein lipase mutations, and cystic fibrosis have important implications for health management. The Human Genome Project holds the promise of many more examples of medically efficacious genetic diagnostic determinations. The recent discovery of the breast cancer associated gene (BRCA-1) has highlighted both the importance of screening individuals for predisposition to a disease, and also for the attendant need for accurate, precise, reproducible, and controlled nucleic acid assays.

Laboratories that perform clinical assays must meet federal and state accrediting agencies' requirements for quality control tests in order to obtain and maintain accreditation. For example, the National Committee for Clinical Laboratory Standards (NCCLS) specifies that quality control samples must be analyzed during every batch of patient specimens analyzed. The federal Clinical Laboratory Improvement Act of 1988 (CLIA '88) mandates similar requirements, as do inspection agencies from most states. The College of American Pathologists (CAP), a non-profit peer inspection group, also requires that quality control samples be analyzed during each analytical run.

In the field of molecular pathology and genetic testing, a quality control sample includes a reference DNA or reference RNA of known sequence quality to evaluate the reliability of all steps of a test. Such reference nucleic acid is ideally as similar as possible to the test sample, and also has broad applicability to all sample preparation and test formats. Additionally, the reference nucleic acid should be easily produced, characterized, and packaged with minimal technical capability.

Materials meeting these requirements, however, are lacking in the field of molecular pathology and genetic testing. This is due in large part to the variety of different technologies and techniques currently employed for a given diagnostic determination. For example, genetic determinations currently include the use of the polymerase chain reaction (PCR), the ligase chain reaction (LCR), branched DNA, allele specific hybridization, and direct sequence determination. In addition, so-called "home brew" produced primer oligonucleotides, and isotopically labeled or non-radioisotopic based probes are used in a variety of configurations in genetic testing, but without any systematic quality control materials, and hence without any validation.

The aforementioned factors, coupled with the lability of nucleic acids, make it virtually impossible to obtain standard reagents to qualitatively and/or quantitatively assess the overall accuracy, reliability, and efficiency of the numerous manipulations performed in all phases of a laboratory assay, that is, from sample preparation through diagnostic determination. For example, one commercially available material for use as a control in a DNA assay consists of lyophilized DNA powder to be diluted and used beginning at an amplification step, which is late in the protocol and well after sample preparation. Thus, for the steps preceding amplification there is no material containing reference DNA by which the accuracy, reliability, and efficiency of these steps may be evaluated. An additional drawback in the use of this material is the apparent lack of extraneous nucleotide residues and other milieu representative of that found in normal cellular extracts.

Even a single alteration in the base sequence of a nucleic acid may have severe consequences to a patient undergoing diagnosis of a genetic disease. Because of the importance of such assays, and also because of the wide range and large numbers of molecular diagnostic assays performed, there is a great need for stable reference nucleic acids to monitor test conditions as closely as possible.

The rapid expansion of genetic-based tests has outpaced the development of appropriate reference materials traditionally used to ensure good laboratory practice. Many current quality controls rely on previously tested clinical specimens and naked DNA, and thus suffer from confidentiality issues, risk of infectious disease, inconvenience, and the inability to validate the entire clinical process. Therefore, there is a long felt need in the art for the development of effective nucleic acid testing quality controls that are safe, convenient, and can mimic a test specimen in that they withstand all steps of the nucleic acid testing. The present invention fulfills this need.

BRIEF SUMMARY OF THE INVENTION

The invention includes a stable isolated nucleic acid reference standard. The nucleic acid reference standard comprises an isolated target nucleic acid comprising a known sequence wherein the isolated target nucleic acid is bound with a microparticulate binding agent. And wherein when the isolated target nucleic acid is so bound the isolated target nucleic acid is not substantially detected in a nucleic acid assay.

In one aspect, the binding agent is at least one of a binding agent selected from the group consisting of a liposome, a polyamine, a siliceous compound, a zeolite, a polystyrene, chitin, and chitosan.

In another aspect, the polyamine is nylon.

In a further aspect, the polystyrene is selected from the group consisting of an amine modified polystyrene and a carboxy polystyrene.

In yet another aspect, the siliceous compound is selected from the group consisting of silica gel, fumed silica, a glass particle, diatomaceous earth, and an amine-modified silica.

In yet a further aspect, the zeolite is low alumina zeolyte.

In another aspect, the binding agent is mixed with a solution selected from the group consisting of a solution comprising alcohol, a solution comprising oil, and a solution comprising a wax base.

In a further aspect, the isolated target nucleic acid comprises a known sequence selected from the group consisting of a ribonucleic acid and a deoxyribonucleic acid.

In yet a further aspect, the isolated target nucleic acid comprises a known sequence selected from the group consisting of a linear nucleic acid and a non-linear nucleic acid.

In another aspect, the nucleic acid reference standard is used to assess the proficiency of a nucleic acid assay.

The invention also includes a stable isolated nucleic acid reference standard. The nucleic acid reference standard comprises an isolated target nucleic acid comprising a known sequence wherein the isolated target nucleic acid is bound with a microparticulate binding agent, and wherein when the isolated target nucleic acid is so bound the isolated nucleic acid is not substantially detected in a nucleic acid assay.

The invention includes a method of assessing the proficiency of a nucleic acid assay. The method comprises a) obtaining a test sample; b) preparing a nucleic acid reference standard comprising a target nucleic acid comprising a known nucleic acid sequence and a binding agent; c) assessing the presence or absence of a second nucleic acid in the test sample using a nucleic acid assay; and d) assessing the presence or absence of the known nucleic acid in the nucleic acid reference standard using the nucleic acid assay of (c), wherein detection of the known nucleic acid sequence in (d) is an indication that the nucleic acid assay is proficient.

In one aspect, the nucleic acid reference standard is mixed with the test sample and the presence or absence of the known nucleic acid and the presence or absence of the second nucleic acid in the test sample are assessed.

The invention includes a method of producing a stable isolated nucleic acid reference standard, the reference standard comprising an isolated target nucleic acid comprising a known sequence wherein the isolated nucleic acid is bound with a microparticulate binding agent, and further wherein when the isolated nucleic acid is so bound the isolated target nucleic acid is not substantially detected in a nucleic acid assay. The method comprises contacting the isolated target nucleic acid with the microparticulate binding agent, thereby producing a stable isolated nucleic acid reference standard.

In one aspect, the microparticulate binding agent is at least one of a binding agent selected from the group consisting of a liposome, a polyamine, a siliceous compound, a zeolite, a polystyrene, chitin, and chitosan.

In another aspect, the polyamine is nylon.

In yet another aspect, the polystyrene is selected from the group consisting of an amine modified polystyrene and a carboxy polystyrene.

In a further aspect, the siliceous compound is selected from the group consisting of silica gel, fumed silica, a glass particle, diatomaceous earth, and an amine-modified silica.

In yet a further aspect, the zeolite is low alumina zeolyte.

In another aspect. The binding agent is mixed with a solution selected from the group consisting of a solution comprising alcohol, a solution comprising oil, and a solution comprising a wax base.

In a further aspect, the isolated target nucleic acid comprising a known sequence is selected from the group consisting of a ribonucleic acid and a deoxyribonucleic acid.

In yet a further aspect, the isolated target nucleic acid comprising a known sequence is selected from the group consisting of a linear nucleic acid and a non-linear nucleic acid.

The invention includes a kit for assessing the proficiency of a nucleic acid assay. The kit comprises a stable isolated nucleic acid reference standard comprising an isolated target nucleic acid comprising a known sequence wherein the isolated target nucleic acid is bound with a microparticulate binding agent, and wherein when the isolated target nucleic acid is so bound the isolated target nucleic acid is not substantially detected in a nucleic acid assay. The kit further comprises an applicator, and an instructional material for the use thereof.

The invention includes a kit for producing a nucleic acid reference standard. The kit comprises an isolated target nucleic acid comprising a known sequence and a binding agent. The kit further comprises an applicator, and an instructional material for the use thereof.

In one aspect, the binding agent is at least one of a binding agent selected from the group consisting of a liposome, a polyamine, a siliceous compound, a zeolite, a polystyrene, chitin, and chitosan.

In another aspect, the polyamine is nylon.

In yet another aspect, the polystyrene is selected from the group consisting of an amine modified polystyrene and a carboxy polystyrene.

In a further aspect, the siliceous compound is selected from the group consisting of silica gel, fumed silica, a glass particle, diatomaceous earth, and an amine-modified silica.

In yet a further aspect, the zeolite is low alumina zeolyte.

In another aspect, the kit further comprises a solution selected from the group consisting of a solution comprising alcohol, a solution comprising oil, and a solution comprising a wax base.

In yet another aspect, the isolated target nucleic acid comprising a known sequence is selected from the group consisting of a ribonucleic acid and a deoxyribonucleic acid.

In a further aspect, the isolated target nucleic acid comprising a known sequence is selected from the group consisting of a linear nucleic acid and a non-linear nucleic acid.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

The regions indicated by the arrows labeled "Ctrl" are the areas dotted with PCR product obtained using extracted FV plasmid DNA-nylon nucleic acid reference standard. The other dots are those amplified using DNA extracted from unidentified blood samples and are included for comparison purposes. The upper rows of dots represent signal detecting using a probe specific for wild type FV gene and the lower rows with dots having the same number represent the corresponding signal obtained by probing the sample with a mutant probe.

Figure 2D:
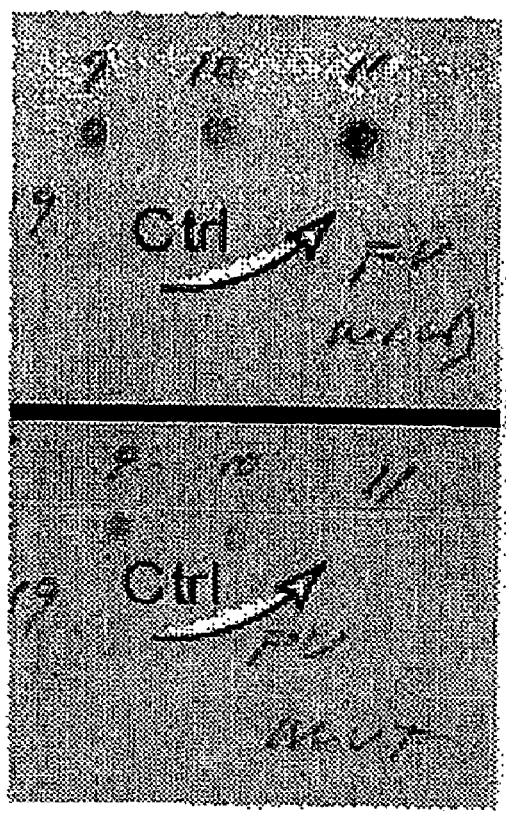
FIG. 2A is an image depicting a dot blot demonstrating detection of Factor V Leiden (FV) mutant and wild type DNA using a nucleic acid reference standard produced 9 days prior to nucleic acid analysis. The dot blot is the product of a clinical laboratory PCR based FV assay aimed at the detection of an FV DNA in blood samples following a DNA extraction and amplification procedure. The data disclosed herein demonstrate detection of nucleic acid reference standard comprising FV plasmid-nylon microparticles following the procedure. The data disclosed herein demonstrate that the construct could be used to detect both mutant FV using a probe specific for mutant FV (Mut Probe) and wild type FV using a probe specific for the wild type sequence (WT Probe) where both assays used a nucleic acid reference standard produced 9 days prior to performing the nucleic acid assay.

FIG. 2B is an image depicting a dot blot demonstrating detection of Factor V Leiden (FV) mutant (Mut Probe) and wild type (WT Probe) DNA using the nucleic acid reference standard produced 26 days prior to nucleic acid analysis. The dot blot is the product of a clinical laboratory PCR based FV assay aimed at the detection of an FV DNA in blood samples following a DNA extraction and amplification procedure. The data disclosed herein demonstrate detection of nucleic acid reference standard comprising FV plasmid-nylon microparticles following the teachings disclosed elsewhere herein using a probe specific for wild type FV (WT Probe) and a probe specific for the mutant FV sequence (Mut Probe). The dot blot assay was performed essentially as described in and using the same sample as depicted in FIGS. 2A, 2C-2G, but the assay was performed 26 days after the nucleic acid reference standard was produced.

FIG. 2C is an image depicting a dot blot demonstrating detection of FV DNA. The dot blot is the product of a clinical laboratory PCR based FV assay aimed at the detection of an FV DNA segment in a FV plasmid-nylon microparticle nucleic acid reference standard following a DNA extraction procedure. The dot blot assay was performed using the same sample as depicted in FIGS. 2A, 2B, 2D-2G, but the nucleic acid reference standard was used in the assay 70 days after it was produced.

FIG. 2D is an image depicting a dot blot demonstrating detection of FV wild type (wild) and mutant (mut) DNA. The dot blot is the product of a clinical laboratory PCR based FV assay aimed at the detection of an FV DNA segment in a FV plasmid-nylon microparticle nucleic acid reference standard following a DNA extraction procedure. The dot blot assay was performed using the same sample as depicted in FIGS. 2A-2C and 2E-2G, but the nucleic acid reference standard was used in the assay 103 days after it was produced.

Figure 2E:
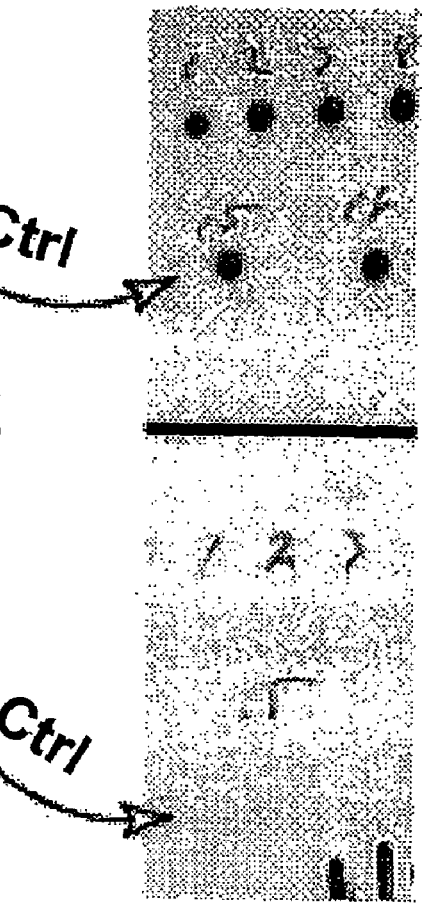

FIG. 2E is an image depicting a dot blot demonstrating detection of FV wild type (top half of the figure) and mutant (bottom half of the figure) DNA. The dot blot is the product of a clinical laboratory PCR based FV assay aimed at the detection of an FV DNA segment in a FV plasmid-nylon microparticle nucleic acid reference standard following a DNA extraction procedure. The dot blot assay was performed using the same sample as depicted in FIGS. 2A-2D and 2F-2G, but the nucleic acid reference standard was used in the assay 151 days after it was produced.

Figure 2F:
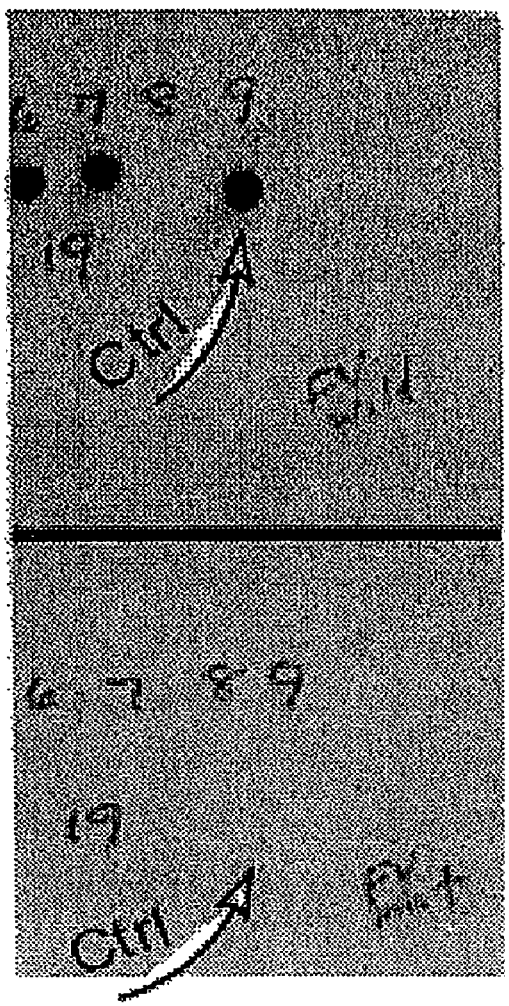

FIG. 2F is an image depicting a dot blot demonstrating detection of FV wild type (wild) and mutant (mut) DNA. The dot blot is the product of a clinical laboratory PCR based FV assay aimed at the detection of an FV DNA segment in a FV plasmid-nylon microparticle nucleic acid reference standard following a DNA extraction procedure. The dot blot assay was performed using the same sample as depicted in FIGS. 2A-2E and 2G, but the nucleic acid reference standard was used in the assay 159 days after it was produced.

Figure 2G:
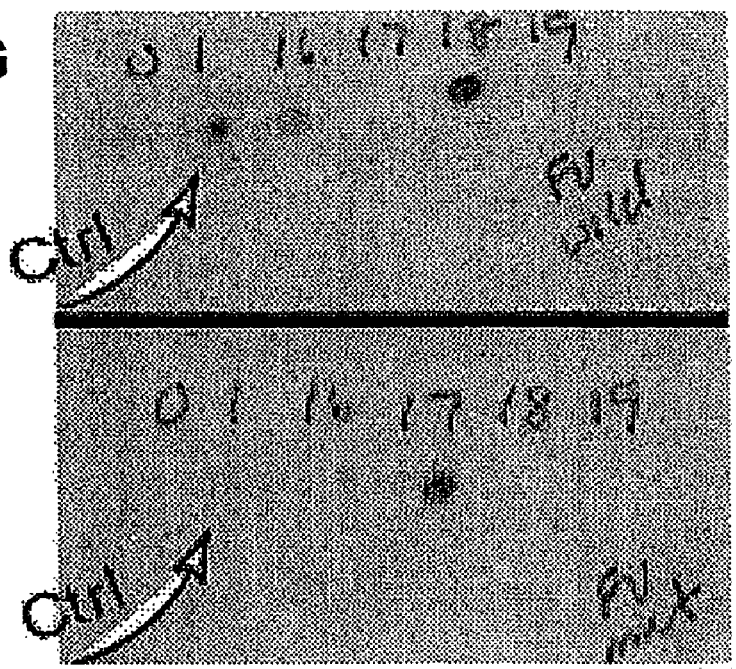

FIG. 2G is an image depicting a dot blot demonstrating detection of FV wild type (wild) and mutant (mut) DNA. The dot blot is the product of a clinical laboratory PCR based FV assay aimed at the detection of an FV DNA segment in a FV plasmid-nylon microparticle nucleic acid reference standard following a DNA extraction procedure. The dot blot assay was performed using the same sample as depicted in FIGS. 2A-2F, but the nucleic acid reference standard was used in the assay 242 days after it was produced.

Figure 3:
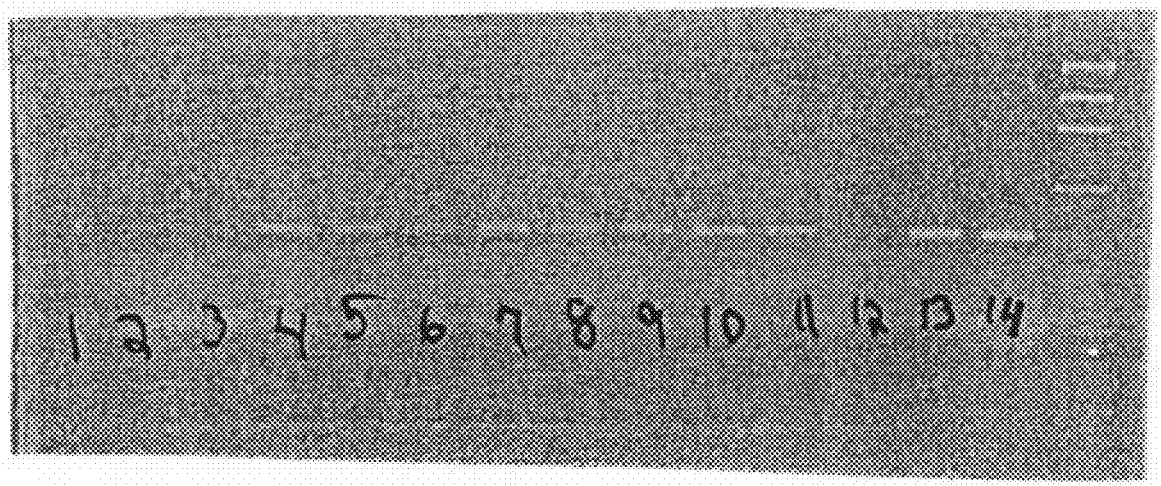

FIG. 3 is an image depicting detection of FV DNA extracted from various nucleic acid reference standards of the invention. Briefly, ethidium bromide staining a gel demonstrated the amplification products produced by a research PCR based FV assay aimed at detection of an FV DNA segment in samples following a DNA extraction process. Lane 1 was a water sample added to the PCR reaction. Lane 2 PCR product was amplified from a 300 µl Gentra puregene extract from 200 mg of autoclaved low surface area nylon microparticles added to 5.6 ng of plasmid FV DNA in 3 ml of 6M guanidine-HCl. Lane 3 PCR product was from a 300 µl Gentra puregene extract from 200 mg of autoclaved low surface area nylon microparticles added to 5.6 ng of plasmid FV DNA in 3 ml of 70% ethanol. Lane 4 PCR product was from a 300 µl Gentra puregene extract from 32 micrograms of autoclaved high surface area nylon microparticles added to 16.8 ng of plasmid FV DNA in 10 ml of storage solution (10% glycerol in 0.025M EDTA solution, v/v, pH 8.7). Lane 5 PCR product was from a 300 µl Gentra puregene extract from 32 micrograms of autoclaved high surface area nylon microparticles added to 16.8 ng of linearized plasmid FV DNA in 10 ml of storage solution (10% glycerol in 0.025M EDTA solution, v/v, pH 8.7). Lane 6 PCR product was from a 300 µl Gentra puregene extract from 21.6 mg of amine modified polystyrene microparticles added to 16.8 ng of plasmid FV DNA in 10 ml of storage solution (10% glycerol in 0.025M EDTA solution, v/v, pH 8.7). Lane 7 PCR product was from a 300 µl Gentra puregene extract from 21.6 mg of amine modified polystyrene microparticles added to 16.8 ng of linearized plasmid FV DNA in 10 ml of storage solution (10% v/v, glycerol in 0.025 M EDTA solution, pH 8.7). Lane 8 PCR product was from a 300 µl Gentra puregene extract from 32 micrograms of autoclaved high surface area nylon microparticles added to 16.8 ng of plasmid FV DNA, washed 2× with 1 ml deionized water and resuspended in 8 ml of 10% glycerol:water solution v/v. A 2 ml solution was then treated with 2 drops of 5N NaOH to yield a solution of pH 10. Lane 9 PCR product was from 300 µl Gentra extract from a 2 ml preparation of liposomes containing 0.7 mg of 1,2-dioleolyl-3-trimethylammonium-Propane, 0.74 mg dipalmitoyl lecithin, 0.16 mg salmon sperm DNA and 18 ng of FV DNA and stored at 4° C. for 5 months before testing. Lane 10 PCR product was from a 300 µl Gentra puregene extract from 72.8 micrograms of autoclaved high surface area nylon microparticles added to 117.5 ng of plasmid FV DNA and 400 microgram of salmon sperm DNA in 10 ml DI water. Lane 11 PCR product was from a 300 µl Gentra puregene extract from 32 micrograms of autoclaved high surface area nylon microparticles added to 16.8 ng of plasmid FV DNA, washed 2× with 1 ml deionized water and resuspended in 8 ml of 10% glycerol in 0.025M EDTA solution, v/v, pH 10.2. Lane 12 is PCR product from a 300 µl water extracted with the Gentra Puregene kit as a check on contamination. Lane 13 is PCR product from a sample of 16.8 ng of plasmid DNA precipitated, washed and reconstituted to 100 microliters. Lane 14 is PCR product from a sample of 16.8 ng of plasmid DNA reconstituted to 100 microliters.

Figure 4:
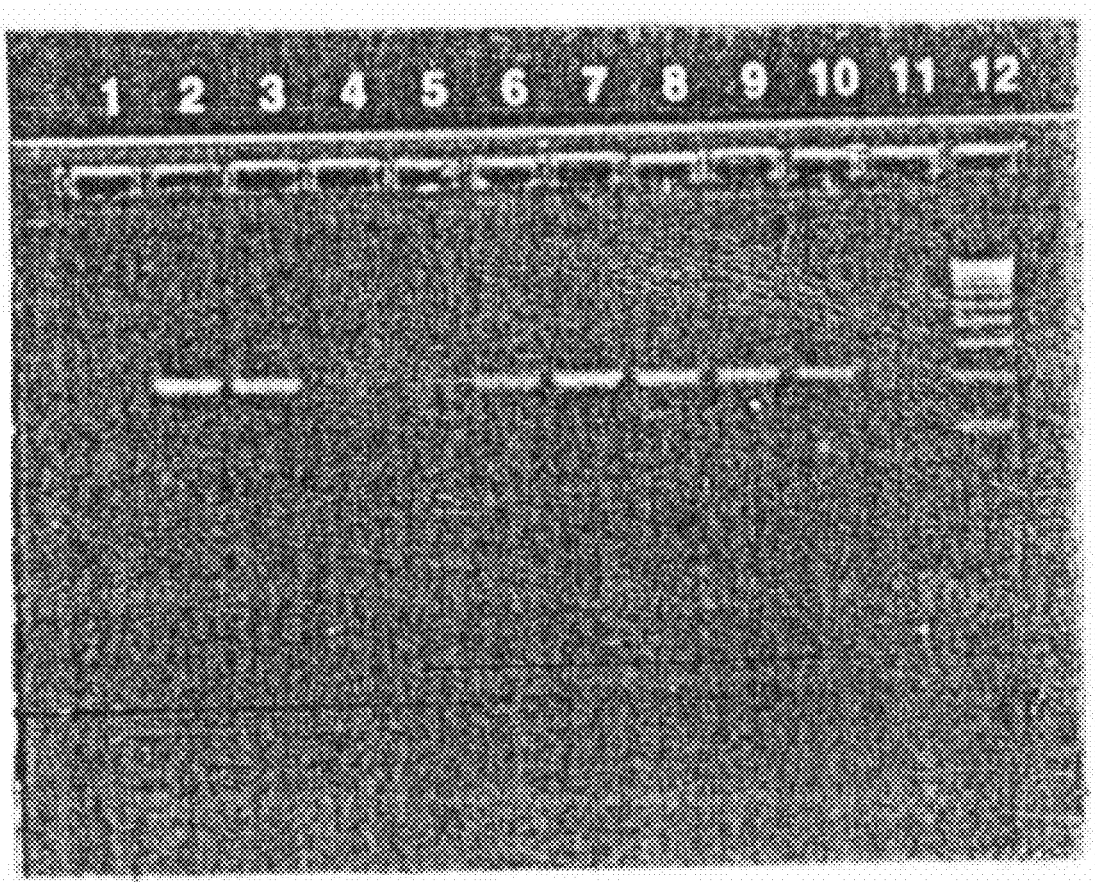

FIG. 4 is an image of an agarose gel stained with ethidium bromide demonstrating detection of FV DNA extracted from a nucleic acid reference standard. The products are the result of the research PCR based FV assay performed on FV plasmid-amine modified polystyrene microparticles, i.e., the nucleic acid reference standard. The amplicons were produced by a research PCR based FV assay aimed at detection of an FV DNA segment in samples following a DNA extraction process. The DNA amplicons depicted in the figure demonstrate embodiments of the invention wherein a nucleic acid reference standard comprising extractable DNA were generated using different DNA levels, and where heating of the sample with extraction reagent is required for DNA release and detection. The gel was 2% agarose and 10 µl of PCR product was added to each lane. The PCR products as amplified products of DNA extracts from sources described below. Three µl of the DNA extracts were added to the PCR reactions. The gel was electrophoresed at 70 mA for 30 minutes. The gel was stained with 0.5 microgram/ml ethidium bromide solution and photographed while illuminated with 230 nM ultraviolet light. Lane 1 was a water sample added to the PCR reaction. Lane 2 PCR product was from a 300 µl Gentra puregene extract from 0.4 micrograms of autoclaved high surface area nylon microparticles added to 16.8 ng of plasmid FV DNA in 3 ml of deionized water. Lane depicts 3 PCR product from a 300 µl Gentra puregene extract from 2.0 micrograms of autoclaved high surface area nylon microparticles added to 16.8 ng of plasmid FV DNA in 3 ml of Deionized water. Lane 4 depicts PCR product from a 300 µl Gentra puregene extract from 6 micrograms of autoclaved high surface area nylon microparticles added to 56 ng of plasmid FV DNA in 2.65 ml of Deionized water. Lane 5 PCR product was from a 300 µl Gentra puregene extract from 50 mg of autoclaved 3 aminopropyl silica microparticles saturated with a solution of 22.5 ng/ml FV plasmid DNA in a 218 µg/ml solution of salmon sperm DNA with a final volume of 1.5 ml. Lane 6 PCR product was from a 300 µl Gentra puregene extract from 54 mg of amine surface polystyrene microparticles saturated with a solution of 22.5 ng/ml FV plasmid DNA in a 218 µg/ml solution of salmon sperm DNA with a final volume of 1.5 ml. Lane 7 PCR product was from 100° C. DNA extraction of the microparticle pellet left from the extraction described in lane 2. Lane 8 PCR product was from 100° C. DNA extraction of the microparticle pellet left from the extraction described in lane 3. Lane 9 PCR product was from 100° C. DNA extraction of the microparticle pellet left from the extraction described in lane 5. Lane 10 PCR product was from 100° C. extraction of the microparticle pellet left from the extraction described in lane 6. Lane 11 PCR product was from extraction of a water sample as a contamination control. Lane 12 was 200 ng of a 100 base pair DNA ladder.

These results demonstrate successful extraction and amplification of DNA from nucleic acid reference standard comprising reference FV plasmid DNA where the binding agents were nylon, 3 aminopropyl silica, and amine functionalized polystyrene. The results demonstrate that DNA is recovered from the nylon and polystyrene based preparations under routine extraction conditions and that DNA could be further recovered from the "extracted" microparticles by heating with cell lysis solution.

Figure 5:
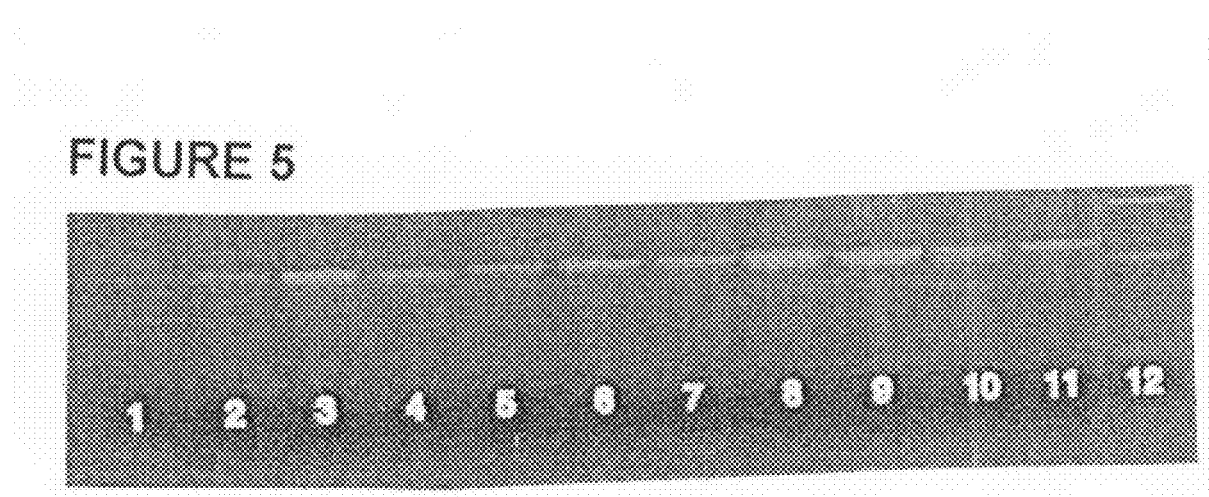

FIG. 5 is an image depicting an ethidium bromide-stained agarose gel demonstrating detection of the amplification products produced using a research PCR based FV assay performed on nucleic acid reference standard comprising FV plasmid and nylon or aminopropyl glass microparticles in the presence of chaotropic salts or alcohol. The amplicons were produced by a research PCR based FV assay aimed at detection of an FV DNA segment in samples following a DNA extraction process. The DNA amplicons depicted in the figure demonstrate embodiments of the invention wherein a nucleic acid reference standards.

Briefly, 3 microliters of DNA extract were added to each PCR reaction, and all lanes contain 10 microliters of PCR product. Lane 1 is a water blank. Lane 2 depicts the PCR amplification product from Gentra puregene extraction of FV plasmid bound to Nylon microparticles in a 6 M sodium iodide solution. Lane 3 depicts the PCR amplification product from Gentra puregene extraction of FV plasmid bound with nylon microparticles in a 70% ethanol solution. Lane 4 depicts the PCR amplification product from Gentra puregene extraction of FV plasmid bound with aminopropyl glass microparticles in a 6 M guanidine hydrochloride solution. Lane 5 depicts the PCR amplification product from Gentra puregene extraction of FV plasmid bound with aminopropyl glass microparticles in a 70% ethanol solution. Lane 6 depicts the PCR amplification product from Gentra puregene extraction of FV plasmid bound with silica gel in conjunction with salmon sperm "filler" DNA in a 100% ethanol solution. Lane 7 depicts the PCR amplification product from Gentra puregene extraction of FV plasmid bound to silica gel in a 100% ethanol solution. Lane 8 depicts the PCR amplification product from Qiagen Spin Column extraction of FV plasmid bound to silica gel in conjunction with salmon sperm "filler" DNA in a 100% ethanol solution. Lane 9 depicts the PCR amplification product from Qiagen Spin Column extraction of FV plasmid bound with silica gel a 100% ethanol solution. Lane 10 depicts the PCR amplification product from phenol/chloroform extraction of FV plasmid bound with silica gel in conjunction with salmon sperm "filler" DNA in a 100% ethanol solution. Lane 11 depicts the PCR amplification product from phenol/chloroform extraction of FV plasmid bound with silica gel in a 100% ethanol solution. Lane 12 is a 100 base pair DNA ladder.

Figure 6:
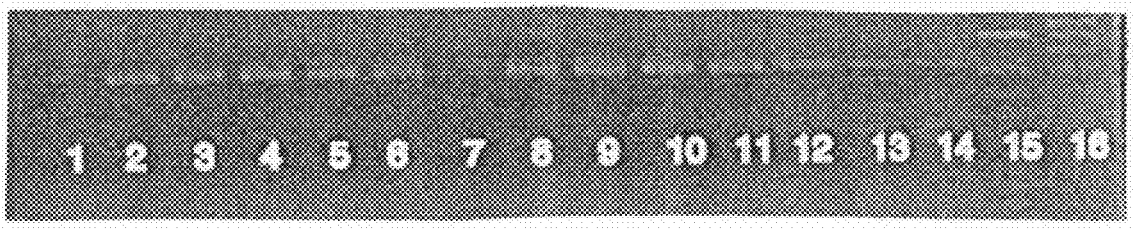

FIG. 6 is an image of a 2% agarose gel stained using ethidium bromide depicting amplification products of the research PCR based FV assay performed on nucleic acid reference standard comprising FV DNA-silica gel microparticles in an alcohol suspension. The amplicons were produced by a research PCR based FV assay aimed at detection of an FV DNA segment in samples following a DNA extraction process. The DNA amplicons depicted in the figure demonstrate embodiments of the invention wherein a nucleic acid reference standard, 4 microliters of DNA extract, were added to each PCR reaction and all lanes contain 10 microliters of PCR product. Lane 1 is a water blank included in the PCR run for quality control purposes. Lane 2 depicts the PCR amplification product from Gentra puregene extraction of FV plasmid bound with silica microparticles in a sodium acetate, acetic acid, isopropanol solution. Lane 3 depicts the PCR amplification product from Gentra puregene extraction of FV plasmid and salmon sperm DNA bound with silica microparticles in a sodium acetate, acetic acid, isopropanol solution. Lane 4 depicts the PCR amplification product from Gentra puregene extraction of FV plasmid DNA bound with low silica zeolite microparticles in a sodium acetate, acetic acid, isopropanol solution. Lane 5 depicts the PCR amplification product from Gentra puregene extraction of FV plasmid DNA bound with silica microparticles in a sodium acetate, acetic acid, isopropanol:glycerol solution. Lane 6 depicts the PCR amplification product from Gentra puregene extraction of FV plasmid complexed with chitosan and bound with silica microparticles in a sodium acetate, acetic acid, isopropanol solution. Lane 7 depicts the PCR amplification product from a water sample carried through the DNA extraction for quality control purposes. Lane 8 is a companion to the experiment in lane 2 and depicts the PCR amplification product from DNA recovered from the RBC lysis supernatant of the Gentra puregene extraction of FV plasmid bound to silica microparticles in a sodium acetate, acetic acid, isopropanol solution. Lane 9 is a companion to the experiment in lane 3 and depicts the PCR amplification product from DNA recovered from the RBC lysis supernatant of the Gentra puregene extraction of FV plasmid and salmon sperm DNA bound to silica microparticles in a sodium acetate, acetic acid, isopropanol solution. Lane 10 is a companion to the experiment in lane 4 and depicts the PCR amplification product from DNA recovered from the RBC lysis supernatant of the Gentra puregene extraction of FV plasmid DNA bound to low silica zeolite microparticles in a sodium acetate, acetic acid, isopropanol solution. Lane 11 is a companion to the experiment in lane 5 and depicts the PCR amplification product from DNA recovered from the RBC lysis supernatant of the Gentra puregene extraction of FV plasmid DNA bound to silica microparticles in a sodium acetate, acetic acid, isopropanol:glycerol solution. Lane 12 is a companion to the experiment in lane 6 and depicts the PCR amplification product from DNA recovered from the RBC lysis supernatant of the Gentra puregene extraction of FV plasmid complexed with chitosan and bound to silica microparticles in a sodium acetate, acetic acid, isopropanol solution. Lane 13 depicts the PCR amplification product from Gentra puregene extraction of FV plasmid dissolved in water. Lane 14 is a companion to the experiment in lane 13 and depicts the PCR amplification product from DNA recovered from the RBC lysis supernatant of the Gentra puregene extraction of FV plasmid dissolved in water. Lane 15 is a DNA ladder (Invitrogen, Carlsbad, Calif.) and lane 16 is a 100 base pair DNA ladder.

Figure 7:
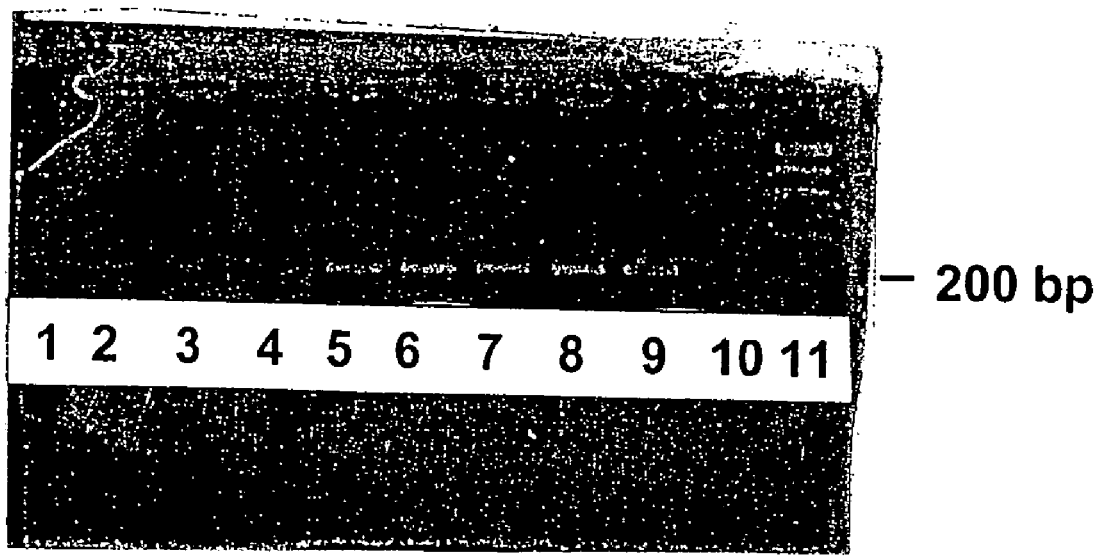

FIG. 7 is an image of an ethidium-bromide stained agarose gel depicting the amplification products of a research PCR based FV assay which was performed on samples similar to those depicted in FIG. 6, supra, except that DNA extraction was performed using the QIAgen spin column method per the manufacturer's instructions.

Figure 8:
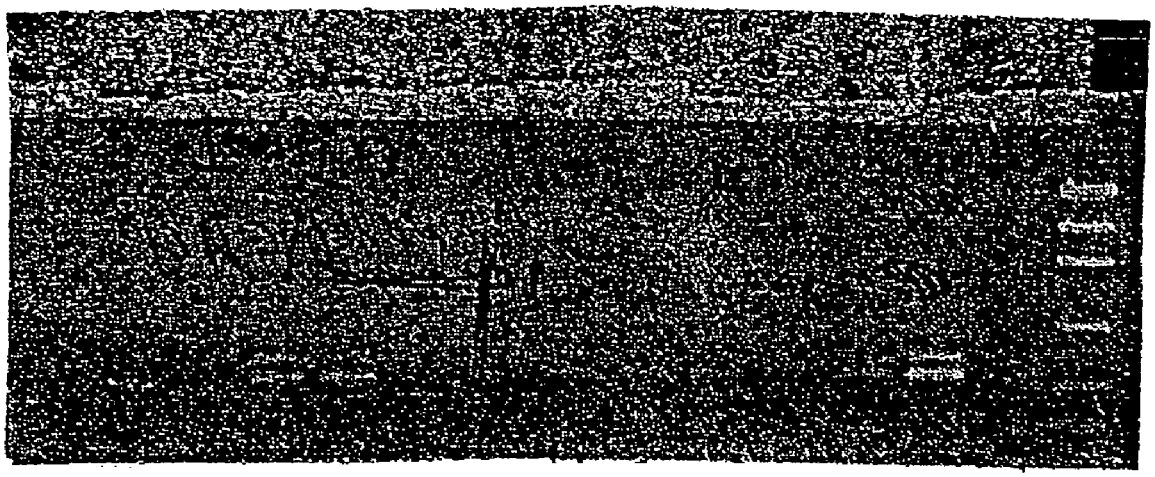

FIG. 8 is an image of an ethidium-bromide stained agarose gel. The image depicts the amplification products detected using a research PCR based FV assay which was performed on samples similar to those in FIG. 6, supra, except that DNA extraction was performed using the phenol-chloroform method.

FIG. 9 is a diagram setting forth the nucleic acid sequence of human factor V Leiden mutant region (SEQ ID NO:7) (GenBank Accession No. Z99572).

DETAILED DESCRIPTION OF THE INVENTION

The present invention relates to synthetic, stable nucleic acid reference standards that can be used to assess the proper processing of biological samples in nucleic acid-based assays. The reference standard represents a vast improvement over prior art standards in that, among other things, it circumvents the need for patient-derived biological materials that may be rare and infectious and/or the use of which may pose ethical considerations. Further, the nucleic acid reference standard of the invention is stable even after prolonged storage and can be used in field conditions under which biological material-based reference standards cannot be used as a control.

Moreover, the nucleic acid reference standard disclosed herein presents an important improvement over prior art standards in that when the target nucleic acid comprised therein is bound with a binding agent, the target nucleic acid behaves like the cellular or viral-derived material which is being queried in the assay in that the nucleic acid reference of the invention both behaves like a microparticulate, e.g., it can be concentrated using centrifugation, and the target nucleic acid is not substantially detected when it is associated with the binding agent. Thus, the nucleic acid reference standard of the invention mimics the biological material being queried wherein a nucleic acid must be separated from the cellular/viral components such as, but not limited to, proteins and lipids, which otherwise inhibit detection of the nucleic acids contained therein. These are important improvements over prior art reference standards which are more fully disclosed and demonstrated as follows.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the term "adjacent" is used to refer to nucleotide sequences which are directly attached to one another, having no intervening nucleotides. By way of example, the pentanucleotide 5'-AAAAA-3' is adjacent the trinucleotide 5'-TTT-3' when the two are connected thus: 5'-AAAAATTT-3' or 5'-TTTAAAAA-3', but not when the two are connected thus: 5'-AAAAACTTT-3'.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |

| Full Name | Three-Letter Code | One-Letter Code |
|---|---|---|
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By the term "applicator" as the term is used herein, is meant any device including, but not limited to, a hypodermic syringe, a pipette, and the like, for administering a nucleic acid, a binding agent, and the like, in a sample.

"Biological sample," as that term is used herein, means a sample obtained from an animal that can be used to assess the presence, absence and/or level, of a nucleic acid. Such a sample includes, but is not limited to, a blood sample, a semen sample, a hair sample, a nail sample, a brain sample, a kidney sample, an intestinal tissue sample, a tongue tissue sample, a heart tissue sample, a mammary gland tissue sample, a lung tissue sample, an adipose tissue sample, a muscle tissue sample, and any sample obtained from an animal that can be assayed for the presence or absence of a nucleic acid.

By the term "binding agent," as used herein, is meant any microparticulate based compound which can bind with a target nucleic acid and which when bound prevents the nucleic acid from being detected in a nucleic acid assay compared with detection of otherwise identical target nucleic acid which is not bound to the binding agent. That is, although the target nucleic acid bound with the microparticulate binding agent can hybridize with a complementary nucleic acid, the target nucleic acid cannot be detected because, inter alia, any nucleic acid amplification reaction required for detection is inhibited by most of the binding agents or solution components. Thus, the reference standard of the invention mimics a cell, virus, or nuclear capsule in that a cell, virus, or nuclear capsule retains much of it's nucleic acid until it is released by rupture of the cell, virus, or nuclear membrane by, among other things, exposure to organic solvents, and detergent and heat whereas, in the case of the binding agent, the nucleic acid is released by breaking of the bonding between the binding agent and nucleic acid by exposure to detergent and heat. At that point, the nucleic acid, whether derived from a cell, a virus, a nuclear capsule, or a construct where it was bound with a microparticulate binding agent, is physically separated from the cellular or viral milieu (or from the binding agent) by filtration or centrifugation.

The skilled artisan, armed with the teachings provided herein, would understand that two things are necessary for detection of a nucleic acid associated with a microparticulate binding agent as disclosed herein: the nucleic acid is separated from the binding agent under conditions of cellular, viral, or nuclear lysis to the degree that the lysis steps are necessary for full separation of the nucleic acid from the agent and the nucleic acid is separated from cellular or other milieu or solvents used in the nucleic acid extraction and purification process. The fact that the cellular milieu, and the milieu accompanying the reference nucleic acid of the invention, contains material that inhibits a PCR reaction, is important is a more secondary point.

Further, a binding agent of the invention encompasses any compound which can bind with a target nucleic acid and which when bound substantially retains the nucleic acid in a hypotonic solution and releases the nucleic acid when exposed to detergent solution or detergent and heat or other nucleic acid extraction media such as, but not limited to, an organic solvent (e.g., chloroform, phenol, and the like, and any combination thereof).

Based on the disclosure provided herein, the skilled artisan would appreciate that the binding agent of the invention includes, among other things, a wide plethora of compounds including cationic lipids, liposomes, polyamines (e.g., nylon), siliceous compounds (e.g., silica gel, fumed silica, diatomaceous earth, glass particles, amine-modified silica, and the like), zeolites (e.g., low alumina zeolyte), polystyrene (e.g., amine-modified polystyrene, carboxy-polystyrene particles, and the like), glucosamines and modified glucosamines (e.g., chitin, chitosan), and combinations of these compounds.

"Clinical Laboratory" means a facility for the biological, microbiological, serological, chemical, immunohematological, hematological, biophysical, cytological, pathological, or other examination of materials derived from the human body for the purpose of providing information for the diagnosis, prevention, or treatment of any disease or impairment of, or the assessment of the health of, human beings. These examinations also include procedures to determine, measure, or otherwise describe the presence or absence of various substances or organisms in the body. Facilities only collecting or preparing specimens (or both), or only serving as a mailing service and not performing testing, are not considered laboratories.

"Clinical laboratory test" and "clinical test," as these terms are used interchangeably herein, essentially follow the CLIA '88 definition: Procedures to determine, measure, or otherwise describe the presence or absence of various substances or organisms in the body through examination of materials derived from the human body for the purpose of providing information for the diagnosis, prevention, or treatment of any disease or impairment of, or the assessment of the health of, human beings.

By "complementary to a portion or all of the nucleic acid encoding a target sequence" is meant a sequence of nucleic acid which does not encode a target sequence. Rather, the sequence which is being expressed in the cells is identical to the non-coding strand of the nucleic acid encoding a target sequence.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g. amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in-vitro expression system. Expression vectors include all those known in the art, such as cosmids, plasmids (e.g., naked or contained in liposomes) and viruses (e.g., retroviruses, adenoviruses, and adeno-associated viruses) that incorporate the recombinant polynucleotide.

A first region of an oligonucleotide "flanks" a second region of the oligonucleotide if the two regions are adjacent one another or if the two regions are separated by no more than about 1000 nucleotide residues, and preferably no more than about 100 nucleotide residues.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

A "genomic DNA" is a DNA strand which has a nucleotide sequence homologous with a gene. By way of example, both a fragment of a chromosome and a cDNA derived by reverse transcription of a mammalian mRNA are genomic DNAs.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

In addition, when the terms "homology" or "identity" are used herein to refer to the nucleic acids and proteins, it should be construed to be applied to homology or identity at both the nucleic acid and the amino acid sequence levels.

A first oligonucleotide anneals with a second oligonucleotide with "high stringency" or "under high stringency conditions" if the two oligonucleotides anneal under conditions whereby only oligonucleotides which are at least about 60%, more preferably at least about 65%, even more preferably at least about 70%, yet more preferably at least about 80%, and preferably at least about 90% or, more preferably, at least about 95% complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, *Molecular Cloning: A Laboratory Manual*, Cold Spring Harbor Laboratory, New York).

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example, at the National Center for Biotechnology Information (NCBI) world wide web site having the universal resource locator "www<dot>ncbi<dot>nlm<dot>nih<dot>gov". BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein.

To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See locator "www<dot>ncbi<dot>nlm<dot>nih<dot>gov".

The percent identity between two sequences can be determined using techniques similar to those described above, with or without allowing gaps. In calculating percent identity, typically exact matches are counted.

As used herein, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins of the invention from other species (homologs), which have a nucleotide sequence which differs from that of the mouse proteins described herein are within the scope of the invention. Nucleic acid molecules corresponding to natural allelic variants and homologs of a cDNA of the invention can be isolated based on their identity to mouse nucleic acid molecules using the mouse cDNAs, or a portion thereof, as a hybridization probe according to standard hybridization techniques under stringent hybridization conditions.

As used herein, an "instructional material" includes a publication, a recording, a diagram, or any other medium of expression which can be used to communicate the usefulness of the nucleic acid, peptide, and/or composition of the invention in the kit for use in a nucleic acid assay and/or to produce a nucleic acid reference standard as disclosed herein. Optionally, or alternately, the instructional material may describe one or more methods of producing a nucleic acid reference standard comprising admixing a nucleic acid with a binding agent. Further, the instructional material can describe use of such nucleic acid reference standard in a nucleic acid assay as described elsewhere herein. The instructional material of the kit of the invention may, for example, be affixed to a container which contains the nucleic acid, binding agent, and/or composition of the invention or be shipped together with a container which contains the nucleic acid, binding agent, and/or composition. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

"Marker gene", as used herein, encompasses a gene in an expression vector that is situated close to target DNA whereby expression of the marker gene indicates the insertion of the target DNA in the expression vector.

The term "nucleic acid construct," as used herein, encompasses DNA and RNA sequences encoding the particular gene or gene fragment desired, whether obtained by genomic or synthetic methods.

By the term "nucleic acid preparation" is meant that a DNA or RNA fragment of interest, or equivalently, the base sequence for which the patient sample is being assayed, is obtained using standard molecular biology techniques and protocols knowledgeable to one skilled in the art. Such techniques will not be repeated herein but are set forth in detail in Sambrook et al. (1989, In: Molecular Cloning-A Laboratory Manual, $2^{nd}$ edition, Cold Spring Harbor Laboratory Press, New York), the disclosure of which is hereby incorporated by reference. A DNA fragment of interest may be custom-synthesized using a variety of commercially available methods and instruments known to one skilled in the art.

"Nucleic acid reference standard," as the term is used herein, encompasses all nucleic acid-based, i.e., comprising a nucleic acid where the nucleic acid is detected based on its sequence, quality control standards comprising a nucleic acid (e.g., RNA and DNA) comprising a known sequence bound with a binding-agent such that the nucleic acid is not detected using methods based on detection of a nucleic acid sequence when compared with detection of the nucleic acid when it is not bound with the binding agent. Thus, the nucleic acid is not detected when bound with the binding agent but can be detected once it is extracted from the binding agent where extraction is performed using nucleic acid extraction methods disclosed herein or methods well-known in the art.

By the terms "nucleic acid test", "nucleic acid assay," or "molecular tests," is meant procedures to determine, measure, or otherwise describe the presence or absence of various nucleic acids and nucleic acid sequences through examination of materials derived from the environment, from organisms, from an animal or from a human body.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

Preferably, when the nucleic acid encoding the desired protein further comprises a promoter/regulatory sequence, the promoter/regulatory is positioned at the 5' end of the desired protein coding sequence such that it drives expression of the desired protein in a cell. Together, the nucleic acid encoding the desired protein and its promoter/regulatory sequence comprise a "transgene."

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "polyadenylation sequence" is a polynucleotide sequence which directs the addition of a poly A tail onto a transcribed messenger RNA sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Reactive," as in "reactive nylon," refers to a substance having a high surface area or a high charge density giving it an avidity and/or binding capacity for nucleic acid.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, Methods for General and Molecular Bacteriology, American Society for Microbiology, Washington, D.C., p. 574).

A "restriction site" is a portion of a double-stranded nucleic acid which is recognized by a restriction endonuclease.

A portion of a double-stranded nucleic acid is "recognized" by a restriction endonuclease if the endonuclease is capable of cleaving both strands of the nucleic acid at the portion when the nucleic acid and the endonuclease are contacted.

By the term "specifically binds," as used herein, is meant a compound, e.g., a protein, a nucleic acid, an antibody, and the like, which recognizes and binds a specific molecule, but does not substantially recognize or bind other molecules in a sample.

A first oligonucleotide anneals with a second oligonucleotide "with high stringency" if the two oligonucleotides anneal under conditions whereby only oligonucleotides which are at least about 75%, and preferably at least about 90% or at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, Molecular Cloning: A Laboratory Manual, Cold Spring Harbor Laboratory, New York).

As used herein, the term "transgene" means an exogenous nucleic acid sequence which exogenous nucleic acid is encoded by a transgenic cell or mammal.

A "recombinant cell" is a cell that comprises a transgene. Such a cell may be a eukaryotic cell or a prokaryotic cell. Also, the transgenic cell encompasses, but is not limited to, an embryonic stem cell comprising the transgene, a cell obtained from a chimeric mammal derived from a transgenic ES cell where the cell comprises the transgene, a cell obtained from a transgenic mammal, or fetal or placental tissue thereof, and a prokaryotic cell comprising the transgene.

By the term "exogenous nucleic acid" is meant that the nucleic acid has been introduced into a cell or an animal using technology which has been developed for the purpose of facilitating the introduction of a nucleic acid into a cell or an animal.

By "tag" polypeptide is meant any protein which, when linked by a peptide bond to a protein of interest, may be used to localize the protein, to purify it from a cell extract, to immobilize it for use in binding assays, or to otherwise study its biological properties and/or function.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of a protein or nucleic acid encoding a protein, to a cell and/or a patient, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; International Patent Application No. WO94/17810, published Aug. 18, 1994; International Patent Application No. WO94/23744, published Oct. 27, 1994).

"Performance characteristic" means a property of a test that is used to describe its quality, e.g., accuracy, precision, analytical sensitivity, analytical specificity, reportable range, reference range, etc.

"Performance specification" means a value or range of values for a performance characteristic, established or verified by the laboratory, that is used to describe the quality of patient test results.

"Referee laboratory" means a laboratory currently in compliance with applicable CLIA requirements, that has had a record of satisfactory proficiency testing performance for all testing events for at least one year for a specific test, analyte, subspecialty, or specialty and has been designated by an HHS approved proficiency testing program as a referee laboratory for analyzing proficiency testing specimens for the purpose of determining the correct response for the specimens in a testing event for that specific test, analyte, subspecialty, or specialty.

"Reference range" means the range of test values expected for a designated population of individuals, e.g., 95 percent of individuals that are presumed to be healthy (or normal).

"Sample" in proficiency testing means the material contained in a vial, on a slide, or other unit that contains material to be tested by proficiency testing program participants. When possible, samples are of human origin.

The nucleic acid reference standard of the invention is "stable" in that it can be maintained at room temperature for a prolonged period without significant loss of signal when the presence of a nucleic acid sequence present in the standard is assessed compared with the identical nucleic acid which is not bound with a binding agent.

"Reference nucleic acid" encompasses all DNA and RNA used for validation, standardization, quality control, and quality assurance purposes in molecular screening and diagnostic assays in manual, automated, kit and non-kit forms, and includes standards, controls, and calibrators.

By the term "substantially detected" in a nucleic acid assay, as used herein, is meant that the target nucleic acid, when bound with a binding agent, is either not detected or is detected at a lower level when compared to an otherwise identical target nucleic acid which is not bound with the binding agent. For instance, the target nucleic acid bound with a binding agent may give a weaker, or no detectable signal upon PCR amplification of the target nucleic acid sequence when compared with the PCR amplification detected in an otherwise identical assay using the same target nucleic acid which is not bound with the binding agent. CR note The reason it is not detected by PCR is that the binding agent or solvents interfere with the PCR reaction by tying up magnesium or otherwise inhibiting enzyme activity—not primarily because the nucleotide is unavailable. Of course another reason for not detecting the nucleic acid is that it was not extracted from the binding agent in the nucleic acid extraction step and was discarded with the binding agent and never made it into the PCR reaction at all.

The term "target nucleic acid," as used herein, encompasses DNA and RNA having a base sequence containing a known sequence to be analyzed in the test specimen.

Description

I. Nucleic Acid Reference Standard

The present invention includes a stable nucleic acid reference standard. The standard can be used in any nucleic acid-detection method based on detection of a nucleic acid sequence such as, but not limited to, validation, standardization, quality control, proficiency evaluation, quality assurance purposes in molecular screening and diagnostic assays in manual, automated, kit, and non-kit forms, and includes standards, controls, and calibrators.

The nucleic acid reference standard comprises a nucleic acid bound with a binding agent where at least a portion the nucleic acid comprises a known target nucleic acid sequence whose presence can be assessed in a sample. One skilled in the art would appreciate, based upon the disclosure provided herein, that when the binding agent is bound with the nucleic acid, the nucleic acid is not substantially detected compared with detection of the same nucleic acid which is not bound with the binding agent. That is, without being held to any particular theory, when the target nucleic acid is bound with the binding agent, the nucleic acid reference standard mimics a cell and/or virus sample where generally a membrane, coat, and the like, must be lysed and the nucleic acid separated from components that bind therewith and inhibit nucleic acid amplification before the nucleic acid fully accessible for analysis.

The skilled artisan would understand, based upon the disclosure provided herein, that such a nucleic acid reference standard is a vast improvement over prior art standards which are not stable at ambient temperatures or for prolonged periods of storage, and which do not provide a quality control for nucleic acid extraction and detection steps since no extraction is required for their detection.

The nucleic acid reference standard of the invention is stable in that it can be maintained at room temperature for a prolonged period without significant loss of signal when the presence of a nucleic acid sequence present in the standard is assayed compared with the identical nucleic acid which is not bound with a binding agent.

One of ordinary skill in the art would appreciate, based upon the disclosure provided herein, that a wide plethora of target nucleic acid sequences can be used in the nucleic acid reference standard of the invention. Thus, although a nucleic acid sequence encoding a Factor V (FV) protein and a cystic fibrosis transmembrane conductance regulator (CFTR) protein are exemplified herein, the present invention is not limited to these or any other target nucleic acid sequences. Rather, the invention encompasses any nucleic acid whose sequence is known and which can be detected on the basis of that known sequence. Examples of such nucleic acids include, but are not limited to, a nucleic acid obtained from a human factor V Leiden region (SEQ ID NO:7; GenBank Accession No. Z99572), parvovirus B19, *Chlamydia trachomatis*, hepatitis C virus, human immunodeficiency virus, lipoprotein lipase gene, a hereditary hemochromatosis gene, and cystic fibrosis mutant gene as described in, e.g., U.S. Pat. No. 6,074,825 and U.S. Pat. No. 5,994,078.

One skilled in the art would appreciate, based upon the disclosure provided herein that a nucleic acid reference standard for a nucleic acid assay is useful and may be necessary to, among other things:

a) assess the performance of a clinical laboratory test;
b) validate the reagents, equipment, instruments, and procedure for a clinical laboratory test;
c) calibrate the results of a clinical laboratory test;
d) verify the lower limit of detection of a clinical laboratory test; and
e) verify the accuracy of a test over a range of results from high to low.

Typically, a reference material is a material that is tested in a clinical laboratory test, the same test used to test patient specimens, to verify that the test is working as expected. In one aspect, the reference material has components relevant to the test that are similar to those found in a patient specimen and the test may be judged to be validated and its performance judged to be satisfactory if the test on the reference material gives the expected result.

Nucleic acid (NA) useful in a nucleic acid testing (NAT) reference would contain non-specific NA, wild type (wt) NA, NA with known disease related mutations, NA diagnostic for the presence of a microorganism, or a specific number of NA segments of known sequence.

Non-specific NA (a negative control) would be used to determine that the test does or does not give a false positive result. Wt NA or NA with a one or more specific disease related mutations would determine whether 1) the test is able to detect the wt or "normal" NA segment and 2) the test is able to detect the disease related mutation or microorganism. The reference nucleic acid may also contain a specific number of wt or mutant NA segments and are used to verify that the test can accurately detect and measure a specified number of known DNA segments.

Further, the skilled artisan would appreciate, armed with the teachings of the present invention, that the target nucleic acid can comprise various known nucleic acid sequences that are known and that can be assayed. That is, the invention encompasses a target nucleic acid comprising several known nucleic acids from different organisms or different sequences from the same organism or different mutant sequences and wild type sequence from the same gene, where the various target nucleic acids are assembled either contiguously or non-contiguously. The routineer would understand that combinations of various nucleic acids sequences can be used in the nucleic acid reference standard of the present invention regardless of the number or arrangement of the sequences.

Moreover, the present invention encompasses a target nucleic acid comprising RNA, DNA, or both. That is, the invention includes a nucleic acid reference standard comprising a target nucleic acid comprising various nucleic acid sequences where the sequences are contiguous, adjacent, or even where the sequences belong to separate nucleic acids and the combination of nucleic acids is admixed with the binding agent to form the nucleic acid reference standard.

The skilled artisan would understand, based upon the disclosure provided herein, that the invention includes a reference standard comprising a target nucleic acid where the target nucleic acid is DNA complementary to an RNA that is analyzed in a genetic test. Such a construct would be useful to evaluate the RNA-detection part of genetic test and it would also be useful to clone into a vector designed to generate an RNA construct that would in turn be used as a control.

In addition, the nucleic acid reference standard of the present invention encompasses modified nucleic acids such as, but not limited to, PDNA (protein DNA), and other non-DNA agents (e.g., pyrolle family compounds) that are reactive in a genetic test.

Polyamides containing N-methylimidazole (Im) and N-methylpyrrole (Py) amino acids are synthetic ligands that have an affinity and specificity for DNA comparable to those of many naturally occurring DNA binding proteins as reported by Wurtz et al., 2001, Org. Lett. 19:1201-3. The ability of DNA polymerases to recognize non-nucleoside imidazole derivatives in a polymerase chain reaction has been studied by Morales et al. (2000, Biochemistry 39:12979-88). Relating to this invention, the polymers can act as binders for DNA reference sequences alone or in combination with other agents and that similar compounds, alone or in conjunction with DNA or RNA, can serve as a nucleic acid reference standard for DNA testing. These compounds, in addition to reacting with DNA, are stable against nuclease degradation and would serve to protect nucleic acids from nuclease degradation.

One skilled in the art would understand, based upon the disclosure provided herein, that the invention encompasses a nucleic acid reference standard comprising a nucleic acid sequence that is also a sequence being detected in a nucleic acid assay of interest, or the target sequence can be an entirely unrelated sequence being detected solely as a quality control to assess proper sample processing. For instance, the present invention includes using a nucleic acid reference standard comprising a target nucleic acid encoding a portion of wild type Factor V and/or mutant Factor V (e.g., Leiden) as a quality control for a clinical nucleic acid assay to detect mutant Factor V in a patient. Further, the present invention includes using the same nucleic acid reference standard comprising an FV nucleic acid in a nucleic acid assay to detect an unrelated nucleic acid, e.g., a hepatitis C virus nucleic acid. Thus, the target nucleic acid present in the nucleic acid reference standard need not be related to the target nucleic acid being assayed in the nucleic acid assay that the standard is serving as a control for.

The skilled artisan would appreciate, based upon the disclosure provided herein, the wide plethora of nucleic acids can be used as a target nucleic acid to produce the nucleic acid reference standard of the invention. That is, virtually any nucleic acid sequence of interest can be introduced into the construct using the methods disclosed herein to produce the claimed reference standard. More specifically, the invention encompasses a nucleic reference standard comprising a wide plethora of target nucleic acids, including, but not limited to, a methyltetrahydrofolate reductase gene, a beta cystathionase synthetase nucleic acid, nucleic acid related to coagulation factors including Factor II, Factor VII, Factor VIII, and Factor IX, a nucleic acid associated with prothrombin, nucleic acid containing translocations related to hematologic disease including a BCR/abl nucleic acid, and other nucleic acids related to a genetic disease such as those listed in the GENETESTS® database maintained by Hanson et al. That is, many nucleic acid sequences associated with a disease, disorder or condition are described at "www<dot>genetests<dot>org", and the web site provides an extensive list of genetic diseases wherein a mutation has been identified that is associated with the disease ("www<dot>geneclinics<dot>org/profiles/disclaimer-index.html"), while the number of genetic diseases identified which are correlated to a known mutation(s) is expanding every day. Further, the target nucleic acid encompasses both wild type and mutation nucleic acid sequences of the CFTR gene including those set forth at the publicly available web site "www<dot>genet<dot>sickkids<dot>on<dot>ca/cftr", which site is maintained by Lap-Chee Tsui et al.

Therefore, the following discussion, while illustrative, should not be construed to limit the invention in any way. More specifically, the target nucleic acid comprises: exons, introns, or both, of a single gene (e.g., at least one exon of a CFTR gene; BRCA1 and BRCA2 genes); a variety of sequences of interest derived from various organisms (e.g., the fragments can be from various pathogens associated with a single disease or disorder for diagnostic purposes such as, but not limited to, a *Mycobacterium tuberculosis* genome; a *Chlamydia trachomatis* genome; a parvovirus B19 nucleic acid; an HIV genome; a hepatitis C virus genome, or fragments of these); fragments of various nucleic acids the products of which are associated with a disease, disorder or condition (e.g., for a disease, disorder or condition associated with abnormal clotting, the construct can comprise a fragment of a gene encoding a common factor V mutation and a fragment comprising a prothrombin 20210 gene fragment comprising a prothrombin disease-related mutation; and a nucleic acid associated with hereditary hemochromatosis, and a lipoprotein lipase gene,); a series of fragments useful for diagnosis or strain-typing related to tuberculosis; fragments comprising various pathogens associated with a disease, disorder or condition such as those pathogenic organisms that are known to colonize cystic fibrosis patients; and the like.

In sum, the skilled artisan, based upon the disclosure provided herein, could readily design a construct of the invention comprising nucleic acid sequences of interest where the nucleic acid is bound with a microparticulate binding agent such that the bound target nucleic acid is separated from liquid suspension by filtration or centrifugation and is removable from the binding agent by detergent lysis or heat or other processes for nucleic acid extraction and is substantially prevented from being detected unless the target nucleic acid is extracted from the binding agent.

The target nucleic acid bound with the binding agent encompasses both linear and non-linear RNA and/or DNA, RNA and/or DNA relevant to the nucleic acid assay, RNA and/or DNA relevant to more than one nucleic acid assay, and RNA and/or DNA relevant to a nucleic acid assay and filler RNA and/or DNA. The reference nucleic acid (target) directly related to the test often would, in a clinical sample, be accompanied by other cellular constituent DNA and/or RNA. To address this in the synthetic nucleic acid reference standard of this invention, non-target (filler) DNA (e.g., salmon sperm DNA, calf thymus DNA or other DNA) will, as an option, be bound to the binding agent along with the target nucleic acid. The filler DNA raises the nucleic acid content of the sample and in some instances this facilitates nucleic acid precipitation and concentration. Some laboratory tests measure a non-target sequence as an internal quality control for the test. The reference nucleic acid of this product also will optionally contain non-target sequences for internal quality control where this is important to the reference function.

The present invention includes a nucleic acid reference standard where a nucleic acid comprising a target nucleic acid sequence is bound with a binding agent. The binding of the nucleic acid with the binding agent substantially decreases or prevents detection of the nucleic acid using typical nucleic acid detection assays well known in the art and/or disclosed herein when compared to detection of the nucleic acid in the absence of binding with the binding agent.

The skilled artisan, armed with the teachings provided herein, would understand that the present invention encompasses a wide plethora of binding agents. Such binding agents include, but are not limited to, cationic lipids and liposomes as described in Lasic et al. (1997, In: Liposomes in Gene Delivery, pages 113-143, CRC Press LLC, Boca Raton, Fla.), Lee et al. (1996, Human Gene Therapy 7:1701-1717), and U.S. Pat. No. 6,126,965, polyamines (e.g., nylon) (see, e.g., Mansfield et al., 1999, BioTechniques 27:1253-1257; U.S. Pat. No. 6,013,434), siliceous compounds (e.g., silica gel, fumed silica, diatomaceous earth, glass particles, amine-modified silica, and the like) (see, e.g., U.S. Pat. No. 5,808,041; Vogelstein et al., 1979, Proc. Natl. Acad. Sci. USA 76:615-6189), zeolites (e.g., low alumina zeolyte), polystyrene (e.g., amine-modified polystyrene, carboxy-polystyrene particles, and the like), glucosamines and glucosamine derivatives (e.g., chitin, chitosan, and the like), and all the combinations of the above compounds.

Cationic lipids and liposomes bind nucleic acids by electrostatic attraction between the positively charged lipid and the negatively charged nucleic acid. These compounds are widely studied as nucleic acid carriers for gene therapy, providing a protective vehicle for the nucleic acid and a vehicle that can facilitate nucleic acid transport across a cellular membrane. The primary value of these compounds in this invention is their ability to stabilize a reference nucleic acid and carry it through the RBC lysis steps of a nucleic acid test. Polyamines (e.g., nylon) comprise a repeating structure of amine groups that bind to the negative oxygen groups on a nucleic acid backbone. Positively charged nylon membranes are widely used for strongly absorbing nucleic acids on their surface. A subject of this invention was the production of high surface area nylon microparticles that would absorb and stabilize a reference nucleic acid to carry it through the RBC lysis and debris removal steps of a nucleic acid extraction and then release the nucleic acid when presented with cell lysis reagents.

Siliceous compounds (e.g., silica gel, fumed silica, diatomaceous earth, glass particles, amine-modified silica) have all been used as agents in nucleic acid purification. The products are available as high surface area microparticles and techniques and reagents (e.g., chaotropic salts, alcohol) for precipitation, concentration and purification of nucleic acid on their surfaces are well known. A subject of this invention is the selection of high surface area microparticulate siliceous materials, and in combination with salts and/or solvents, to cause a reference nucleic acid to be stabilized to carry it through the RBC lysis and debris removal steps of a nucleic acid extraction and then release the nucleic acid when presented with cell lysis reagents. The use of cationic lipids or glycosamines in conjunction with the siliceous surface to enhance the retention of reference nucleic acid is encompassed in the invention.

Zeolites (e.g., low alumina zeolyte) are known absorbents of organic and inorganic molecules and catalysts for organic reactions. Their siliceous surface with unique pore structures and ion exchange sites render them of interest in nucleic acid binding. They are also available as microparticulates of varying density and surface area.

The invention includes selection of high surface area microparticulate zeolite materials with nucleic acid binding affinity, and, in combination with salts and/or solvents, to cause a reference nucleic acid to be stabilized on the surface to carry it through the RBC lysis and debris removal steps of a nucleic acid extraction and then release the nucleic acid when presented with cell lysis reagents.

Polystyrene (e.g., amine-modified polystyrene, carboxy-polystyrene particles, and the like) are used in commercial products for the separation of nucleic acids from solution. The invention includes the selection of polystyrene microparticles with nucleic acid binding affinity and, in combination with salts and/or solvents, to cause reference nucleic acid to be stabilized on the surface to carry it through the RBC lysis and debris removal steps of a nucleic acid extraction and then release the nucleic acid when presented with cell lysis reagents. The invention further encompasses that the carboxyl polystyrene surface can be readily modified by electrostatic or covalent binding with cationic agents to increase its affinity for nucleic acid entities.

Proteins bind to DNA and are important in protecting and shepherding DNA in biological systems and also in the regulation of genetic expression as described by, for example, Johnson et al. (2001, J. Biol. Chem. May 11, 2001). One skilled in the art would appreciate, based upon the disclosure provided herein, that selected proteins have the ability to stabilize a reference nucleic acid on a microparticulate surface or within suspension and carry it through the RBC lysis steps of a nucleic acid test and then release the nucleic acid when presented with cell lysis reagents.

One skilled in the art would appreciate, based upon the teachings provided herein, that the target nucleic acid, when bound with the binding agent, is not substantially detected in a nucleic acid assay. That is, when compared to an otherwise identical target nucleic acid not bound with a binding agent, the target nucleic acid bound with a microparticulate binding agent must be separated from the binding agent to be fully detected, or is detected to a lesser extent, when assayed in a nucleic acid assay, which assays are known in the art and/or are disclosed herein.

Without wishing to be bound by any particular theory, binding of the target nucleic acid with a binding agent "mimics" a cell or virus particle in that the construct behaves in solution as a microparticulate which can be filtered or, inter alia, sedimented by, e.g., centrifugation or sedimentation at 1×g. Thus, the nucleic acid reference standard, unlike prior art standards relating to unbound, "naked" nucleic acid molecules, offers an important advantage for most nucleic acid assays which involve filtration or centrifugation step(s) in that detection of the target nucleic acid requires that the same steps necessary for isolation and detection of a cell/virion-associated nucleic acid be performed upon the construct of the invention.

Further, the construct mimics a cell/virus particle in that, without wishing to be held to any particular theory, the sample components such as salts, and other components, may interfere with the amplification reaction(s). Thus, the target nucleic acid bound with a binding agent gives a weaker, or no detectable signal, upon PCR amplification of the target nucleic acid sequence when compared with the PRC amplification detected in an otherwise identical assay using the same target nucleic acid which is not bound with the binding agent.

The reference standard of the present invention has numerous advantages over using cellular- or viral-derived material as a standard in that there is a paucity of cell lines comprising the target nucleic acid sequences of interest, especially where the target nucleic acid comprises a rare mutation or variant. Further, use of patient-derived materials presents ethical concerns that are circumvented by using the synthetic reference standards disclosed herein. Patient-derived materials also must be considered potentially infectious and, in some cases, highly dangerous. Moreover, the reference standards of the present invention are stable under normal storage conditions giving a detectable signal many months after they are produced thereby demonstrating that, unlike cell and virus-derived materials requiring sophisticated tissue culture techniques, the reference standard of the invention can be readily used in nucleic acid assays under field conditions where tissue culture facilities are not readily available. Such field use encompasses, but is not limited to, extra-terrestrial applications including use of the reference standard in nucleic acid assays performed at, for instance, a space station or other off-world uses.

II. Methods

A. Method of Assessing Proficiency of Nucleic Acid Assay

A proficiency test is the means by which a laboratory monitors and evaluates its testing methods. Proficiency testing is frequently administered by professional laboratory organizations that send "blind" specimens to subscribing laboratories for testing. The laboratories test for the target compounds (e.g., nucleic acid, protein, lipid) and report the results back to the sponsoring group. The proficiency of the testing laboratory is assessed by the accuracy of their results from testing the "blind" specimen. A clinical laboratory will test several proficiency specimens 3 times per year. There is a significant need for nucleic acid reference standards that can be produced in quantity and reliably shipped to testing laboratories as proficiency specimens. The clinical laboratory requirements for proficiency testing are set forth in Medicare, Medicaid and CLIA programs: Regulations implementing the Clinical Laboratory Improvement Amendments of 1988. (CLIA), U.S. Department of Health and Human Services; Final rule. 57:7002-7186).

The present invention further includes a method of assessing the proficiency of a nucleic acid assay. That is, the invention provides a method of determining whether the manipulations and processes (e.g., nucleic acid extractions, nucleic acid isolation, amplification reaction, detection reaction, and the like, see also FIG. 1) encompassing a nucleic acid assay have been performed properly.

The method comprises using a nucleic acid reference standard of the invention to determine whether the nucleic acid assay was performed properly. This is because, as more fully set forth elsewhere herein, the nucleic acid reference standard disclosed herein allows the determination of whether the nucleic acid manipulation steps of an assay have been carried out properly, in that a positive signal will result only if the steps were performed properly. More specifically, the nucleic acid reference standards disclosed herein allow the determination of whether the nucleic acid extraction step was successful in extracting the nucleic acid whose presence or absence is being assessed, also referred to as the "second nucleic acid," so that it can be detected in the specific detection step.

The skilled artisan would understand, based upon the disclosure provided herein, that the nucleic acid reference standard can be processed parallel with the sample at issue, either contemporaneously or at a different time therewith. Alternatively, the nucleic acid reference standard can be added to the sample being analyzed and can serve as an internal control (either a negative or a positive control, or both) for the sample being processed. In this instance, the target nucleic acid sequence present in the nucleic acid reference standard can be a sequence that is not present in the sample being assayed. Thus, a positive signal demonstrates that the nucleic acid test manipulations have been carried out properly and the nucleic acid reference standard serves as an internal quality control in the assay thus assessing the proficiency of the nucleic acid assay.

The invention encompasses methods where the sequence of the target nucleic acid present in the nucleic acid reference standard is the same or different from the sequence of the second nucleic acid whose absence or presence in a sample is being assessed. Thus, the nucleic acid reference standard can comprise a nucleic acid whose sequence is identical to the sequence of the nucleic acid that is being detected in the sample. Alternatively, the nucleic acid reference standard can comprise a nucleic acid whose sequence is entirely unrelated to the sequence of the nucleic acid which may be present in the sample being queried. The invention also encompasses a nucleic acid reference standard comprising several target nucleic acids having different sequences some or all of which may be the same as or different from the sequences of one or more nucleic acid sequences whose presence or absence is being assessed in the sample being queried.

One skilled in the art would appreciate, based upon the disclosure provided herein, that the nucleic acid assay comprises additional steps which are known in the art or disclosed herein, for the detection of the presence or absence of a nucleic acid of interest in a sample or a change in sequence of a nucleic acid of interest. Examples of the latter include assays for genetically modified organisms and microorganisms that may have developed drug resistance mutations. The invention is not limited to any particular nucleic acid assay protocol, but encompasses a wide plethora of assays known in the art (see, e.g., assays described in Sambrook et al., supra, and Ausubel et al., supra), disclosed herein, or to be developed in the future. Nucleic assay methods wherein the reference materials of this invention are useful encompass basic methodologies and automated versions thereof and variations including sequencing and nucleic acid testing by micro-array technology.

B. Method of Producing a Nucleic Acid Reference Standard

The invention includes a method of producing a nucleic acid reference standard comprising a target nucleic acid bound with a binding agent where binding of the nucleic acid and agent stabilizes the nucleic acid on the agent in solution or suspension and controls its release such that it is substantially carried through the specimen preparation steps of a genetic test and is released in the cell lysis steps.

The skilled artisan would appreciate, based upon the disclosure provided herein, that admixing at least one known nucleic acid sequence of interest with a binding agent (e.g., liposomes as described in Lasic et al. (1997, In: Liposomes in Gene Delivery, pages 113-143, CRC Press LLC, Boca Raton, Fla.) Lee et al., (1996, Human Gene Therapy 7:1701-

1717), and U.S. Pat. No. 6,126,965, polyamines (e.g., nylon) (see, e.g., Mansfield et al., 1999, BioTechniques 27:1253-1257; U.S. Pat. No. 6,013,434), siliceous compounds (e.g., silica gel, fumed silica, diatomaceous earth, glass particles, amine-modified silica, and the like) (see, e.g., U.S. Pat. No. 5,808,041; Vogelstein et al., 1979, Proc. Natl. Acad. Sci. USA 76:615-6189), zeolites (e.g., low alumina zeolyte), polystyrene (e.g., amine-modified polystyrene, carboxy-polystyrene particles, and the like), chitin, chitosan, and the like, can produce the desired nucleic acid reference standard.

Once armed with the teachings of the present invention, including methods of determining the binding capacity of various binding agents, and methods of assessing whether a nucleic acid reference standard produced according to the methods of the invention is useful to detect a nucleic acid of interest, the skilled artisan can produce a wide variety of nucleic acid reference standards by combining a nucleic acid of interest (or various nucleic acids) and a wide plethora of binding agents and assaying whether the nucleic acid reference standard formed has the desired characteristics as set forth elsewhere herein. Thus, although numerous methods are disclosed elsewhere herein, as exemplified in Examples 1-12, below, the invention is not limited to these methods or to the nucleic acids or binding agents disclosed herein. Rather, the present invention includes such reaction conditions, binding agents, and nucleic acid molecules as would be understood by the skilled artisan based upon the disclosure provided herein. Briefly, these include as follows: Nylon, amine modified polystyrene or amine derivatized silica microparticulates or similar agents that have high affinity for DNA are combined in solution directly with the reference DNA. The solution can be adjusted with the addition of chaotropic salts or organic solvents or pH adjustment to decrease the solubility of the DNA. Likewise the solubility of the DNA can be increased by adjustment of pH to neutral or basic in a low salt concentration solvent.

Siliceous materials, polystyrene, zeolites, low alumina zeolites, glass, glass fiber microparticulates are combined with reference DNA in a manner to precipitate the DNA on to the particulate. The DNA may be absorbed directly on to the microparticulate or may be added to an alcohol or chaotropic salt based suspension of the microparticulates. The final suspension may be adjusted with buffered solution and organic solvent to cause the DNA to remain bound to the microparticulate.

Hydrophobic forms of silica microparticles, produced by treatment with organosilanes, can be combined with reference DNA in the same manner. Further stabilization of the DNA on the microparticle can be accomplished by incorporating the microparticulate-DNA product into oil or wax droplets or a layer of oil or wax fluid. Using a heavier than water oil or wax causes the microparticle:DNA:oil mixture to precipitate on standing and to form emulsions when vigorously mixed.

The avidity of binding of DNA on a microparticulate surface can be increased by the coprecipitation of DNA on to a surface with a DNA binding compound such as polylysine, polyethylene amine, protein, or chitosan. This is accomplished by mixing the DNA binding compound in solution with the DNA and then absorbing the product on to a microparticle according to one of the processes described above.

In sum, once armed with the teachings of the present invention, including but not limited to the fact that nucleic acids bound with certain binding agents can perform as nucleic acid reference standards in nucleic acid assays, the skilled artisan would be able to determine the reaction conditions (solvents, salts, temperatures, and the like), necessary to produce the claimed nucleic acid reference standards.

III. Kits

The invention includes various kits comprising the nucleic acid reference standard of the invention, an applicator, and instructional materials which describe use of the compound to perform the methods of the invention. Also included are kits for producing the nucleic acid reference standards, such kits including reagents for admixing nucleic acids and binding agents as disclosed herein. Although exemplary kits are described below, the contents of other useful kits will be apparent to the skilled artisan in light of the present disclosure. Each of these kits is included within the invention.

In one aspect, the invention includes a kit for assessing the proficiency of a nucleic acid assay. The kit is used pursuant to the methods disclosed in the invention. Briefly, the kit may be used to assess whether the various steps of the assay have been performed properly and successfully by testing the nucleic acid reference standard provided in the kit beside patient specimens in the assay whose proficiency is being assessed. Moreover, the kit comprises an applicator and an instructional material for the use of the kit. These instructions simply embody the examples provided herein.

The invention also includes a kit for producing a nucleic acid reference standard. The kit is used pursuant to the methods disclosed in the invention. Briefly, the kit can be used to produce a nucleic acid of interest bound with a binding agent provided in the kit where the nucleic acid and the agent are contacted and allowed to bind according to the conditions disclosed in the invention, or under such conditions as would be apparent to the skilled artisan based upon the teachings of the invention.

The kit comprises an isolated target nucleic acid comprising a known sequence of interest and a binding agent. The kit further comprising an applicator, and an instructional material for the use thereof.

The invention includes a kit that further comprises a binding agent is at least one of a binding agent selected from the group consisting of a liposome, a polyamine, a siliceous compound, a zeolite, a polystyrene, chitin, and chitosan. In one aspect, the polyamine is nylon, as exemplified herein, but the invention is not limited to solely nylon as a polyamine. Other polyamines and related compounds, such as, but not limited to, can include spermine, polyornithine, polylysine, and lipospermines.

Similarly, the invention includes a kit comprising a polystyrene, wherein the polystyrene can be an amine modified polystyrene and a carboxy polystyrene. Further, the kit can comprise a siliceous compound which is selected from silica gel, fumed silica, glass particles, diatomaceous earth, and amine-modified silica.

Moreover, the invention includes a kit wherein the zeolite is low alumina zeolyte.

In addition to kits comprising nucleic acids and binding agents, the invention encompasses kits further comprising solutions useful for binding the nucleic acid and the binding agent. Such kits include those comprising a solution selected from the group consisting of a solution comprising buffered deionized water, chaotropic salt solutions, alcohols, a solution comprising oil, and a solution comprising a wax base and solutions or mixtures comprising combinations of the above. A description of how these solutions are useful for nucleic acid binding is given above in the discussion on binding agents and their use.

The nucleic acid reference standard, in order to serve as a control for the laboratory test, is required to mimic a patient specimen in the DNA extraction and testing process. This requires that the bound nucleic acid be substantially retained on or within the binding agent through the specimen preparation steps (i.e. the digest or suspension and RBC lysis steps) of a nucleic acid extraction and to release its nucleic acid upon treatment with detergent and/or heat in the cell lysis step. The preparation of the a nucleic acid reference standard involves use of a combination of microparticulates, nucleic acid binding agents and solvent or solutions that result in the desired degree of DNA binding.

As disclosed previously elsewhere herein, the use of alcohol or chaotropic salts can result in the increased retention of DNA in the RBC lysis steps of a reaction and yet release the DNA when subjected to the nucleic acid extraction step. The use of amine derivatized surfaces also results in increased DNA retention. High retention of DNA in the construct is required to mimic the extraction of DNA from a microbacteria such as tuberculosis. In this case the DNA, was extracted after first digesting the protein of the specimen with enzymes followed by heating the specimen with detergent. The retention of DNA in a mild nucleic acid extraction and release of DNA when heating with detergent was observed in a product of this invention wherein FV reference DNA plasmid was complexed with amino propyl glass.

The kits of the invention encompass a kit where the isolated target nucleic acid comprising a known sequence is a ribonucleic acid and/or a deoxyribonucleic acid.

Further, the isolated target nucleic acid comprising a known sequence in the kit is selected from the group consisting of a linear nucleic acid and a non-linear nucleic acid.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Preparation and Testing of Reference DNA Compositions

The experiments presented in this example may be summarized as follows.

The data disclosed herein describe the preparation of novel compositions comprising reference DNA and vector and the use of these compositions to validate the extraction protocol and the DNA detection steps in a clinical genetic assay.

The Materials and Methods used in the experiments presented in this example are now described.

Preparation of Nylon Microparticles as a Vector

Production of microparticles for use as solid support for immunoassay antibodies was described previously (McConway et al., 1986, J. Immunol. Methods 95:259-266). The method was modified for production of microparticles for use a nucleic acid binding agent. More specifically, two grams of Nylon 6/6 pellets (Scientific Polymer Products, 6265 Dean Parkway, Ontario, N.Y. 14519) were dissolved and 100 ml of concentrated hydrochloric acid (HCl) for 10 hours at room temperature. The solution was introduced at a rate of 2 drops per second, 5 ml at a time, into 500 ml aliquots of water in a Sunbeam 4144-8 blender (Sunbeam Products Inc., Fla.) at regular speed.

Nylon microparticles were separated from each aliquot by centrifugation for 10 minutes at 3000×g in a Sorvall GLC2B centrifuge (Sorvall Products, Wilmington, Del.). The microparticles were washed twice in 40 ml aliquots of 0.2 M sodium acetate pH 5.2, and the microparticles were resuspended in deionized water to a total volume of approximately 35 ml and autoclaved. Typical solids content of the final suspension was 40 mg/ml when dried to 100° C. More concentrated solutions were prepared by 7200×g centrifugation, followed by removal of the supernatant and dilution to the desired concentration.

In yet another variation, nylon 6/6 pellets were dissolved in concentrated HCl for times varying from 9 hours to 20 hours at room temperature. The data demonstrated that dissolving the nylon for less than 10 hours resulted in incomplete dissolution and that 17 or more hours of dissolution resulted in nylon strings rather than nylon microparticles. The optimum time was when the nylon was reliably totally dissolved which was between 10 and 14 hours.

In yet a further variation of this procedure the nylon/HCl solution was dropped into a stirred 0.5 N sodium hydroxide solution. This did not prove to be an advantage in the type of microparticle produced.

In another variation, the nylon microparticle solutions were incubated in a 2 M glycine solution as soon as they were formed as a means to cross-link active and unreacted nylon carboxyl groups. The precipitated nylon solid was seen, by light microscopy, to consist of microparticles ranging in size from approximately 1 to 5 microns and agglomerates thereof.

Preparation of FV Plasmid DNA as Reference DNA

Many of the protocols described herein are well-known in the art and can be found in standard treatises such as, e.g., Sambrook et al. (1989, In: Molecular Cloning: A Laboratory Manual, Cold Spring Harbor Laboratory Press, New York) and Ausubel et al. (1997, In: Current Protocols in Molecular Biology, Green & Wiley, New York).

Primers specific for a 515 base pair segment of DNA encoding Factor V (FV) were chosen to encompass target amplicons used in known clinical DNA based assays. The DNA segment was amplified in a standard PCR reaction using the following primers MMQCIFVF1: 5'CTTCG-GCAGTGATGGTACTGA 3' (SEQ ID NO:1), and MMQCIFVR1: 5'TGCAATATTAATTGGTTCCAGC 3' (SEQ ID NO:2).

The FV segment was PCR amplified with Taq polymerase. Fifty microliter PCR reactions were run according to a standard protocol such as those described in, e.g., Sambrook et al. (1989, In: Molecular Cloning: A Laboratory Manual, Cold Spring Harbor Laboratory Press, New York) and Ausubel et al. (1997, In: Current Protocols in Molecular Biology, Green & Wiley, New York). Briefly, PCR cycling conditions were: 94° C. for 5 minutes, 32 cycles of 94° C. for 15 seconds, 63° C. for 15 seconds, 68° C. for 20 seconds, a hold period at 68° C. for 5 minutes and a final hold period at 4° C.

The amplification products were purified using absorption on to a silica membrane at pH 5, followed by a buffered alcohol wash and elution at pH 8.5. Specific amplification products were visualized on 6% polyacrylamide gels by ethidium bromide staining and ultraviolet illumination.

The PCR product was sequenced using cycle sequencing with BigDye Terminators (Applied Biosystems, Foster City, Calif.), using forward and reverse PCR primers. The forward and reverse primers were the same as those used for amplification of the segment, i.e., SEQ ID NOS:1 and 2. Sequence analysis was performed using an ABI Prism 310 capillary electrophoresis analyzer Applied Biosystems, Foster City, Calif. The sequence was found to be correct by comparison with that provided in GenBank Accession Z99572. The amplicon was cloned by ligation into pGEM-T under the following conditions: 5 µl 2× Buffer; 1µ pGEM-T (50 ng/µl); 3 µl amplicon (1 µg); 1 µl T4 Ligase (4 Weiss units/µl).

The reaction was incubated overnight at 4° C. The ligation reaction was purified for electroporation using ammonium acetate buffered alcohol precipitation. Electroporation was performed using the Bio-Rad GenePulser™ (Bio-Rad Laboratories, Richmond, Calif.), followed by 1 hour incubation in SOC medium (Life Technologies, Inc., Rockville, Md.) and plating on Luria Broth (LB)/ampicillin plates using standard methods.

White colonies were picked and cultured in LB/ampicillin media, cells were isolated by centrifugation and resuspended in a 50 mM Tris-HCl, pH 7.5, 10 mM EDTA, 100 ug/ml RNase A solution.

Plasmid from the cells was purified and separated using Promega Wizard®Plus Minipreps DNA Purification System per the manufacturer's instructions (Promega Corp., Madison, Wis.). Briefly, the cells were lysed by adding a volume of Cell Lysis Solution (0.2 M NaOH in 1% sodium dodecyl sulfate [SDS]) and inverting the tube 4 times. The solution was neutralized with 300 µl of 1.32 M KOAc (potassium acetate), pH 4.8, and any debris was removed by centrifugation.

Plasmid was then separated by absorption onto a filter bed of silica and silica fibers in 4.2 M guanidine HCl. The plasmid was washed with 2 ml of wash solution (80 mM potassium acetate, 8.3 mM, Tris-HCl, pH 7.5, 40 µM EDTA, 55% ethanol) and then eluted with 50 µl of nuclease free water. Plasmid from the culture was sequenced in both directions with plasmid based pUC M13 primers using the sequencing conditions and system described above. Sequencing demonstrated that the DNA sequence exactly matched that of the original amplicon.

A three milliliter cell suspension was removed from the culture and was mixed with 2 ml sterile glycerol and aliquots were frozen at −70° C. This was labeled "Fvwtclone: for Factor V wild type clone. The product for use in DNA binding studies was produced by culturing an aliquot of the cloned product. Plasmid was extracted by miniprep as described above. The yield was 24.5 micrograms and the product was stored frozen at a concentration of 490 ng/µl.

Preparation of Reference DNA-Vector Composition

FV plasmid DNA was diluted to 23.5 ng/ml, and salmon sperm DNA was prepared in a solution of 200 µg/ml and Nylon microparticles (1 micron sized reactive nylon 6/6) were prepared in a concentration of 72.8 mg/ml in a 0.2 M sodium acetate, pH 5.2, solution. Three milliliters of the nylon microparticle solution was mixed with 2 ml of single stranded (SS) DNA solution and 5 ml of the FV plasmid DNA solution. This suspension was mixed using a vortexer and stored at 4° C.

DNA Extraction by the Capture® DNA Isolation Kit (Gentra Systems)

DNA extraction by the Capture® DNA Isolation Kit (Gentra Systems, Minneapolis Minn.) was performed according to manufacturer instructions. Briefly, a sample was applied to the purification matrix contained in a spin column. The cells and nuclei are lysed upon contact with the matrix. The DNA was captured on the spin column matrix and protein, heme and other contaminants were eluted. The DNA was released from the matrix by heating with an elution solvent (typically 100 µl of 1×TE buffer, pH 7.5). Samples of purified DNA were ready for analysis and did not require precipitation. The purified DNA solution was compatible with PCR and other DNA analysis procedures.

In the capture method two hundred microliters of sample were added to a resin-containing capture column and were absorbed into the column resin for 1 minute and for up to 1 hour at room temperature. Four hundred microliters of DNA purification solution was added and the mixture was incubated at room temp for 1 minute followed by centrifugation for 10 seconds from about 2000 to 12000×g. The column was washed with another 400 µl of DNA purification solution, incubated for 1 minute at room temperature, followed by centrifugation for 10 seconds at about 2000 to 12000×g. The sample was then washed with 200 µl of DNA elution solution at room temperature and centrifuged for 10 seconds at about 2000 to 12000×g. The sample bound with the resin was treated with 200 µl DNA elution solution, incubated for 10 minutes in dry block heater at 99° C., and the DNA containing solution was recovered by centrifugation for 20 seconds at about 2000 to 12000×g.

DNA Extraction by the Puregene® DNA Isolation Kit (Gentra Systems)

DNA extraction using the Puregene® DNA Isolation Kit (Gentra Systems) was performed according to manufacturers instructions (Gentra Systems, Minneapolis, Minn.). Briefly, 300 microliters of each DNA and microparticle suspension was added to 900 microliters of RBC lysis solution (typically 144 mM ammonium chloride, 1 mM sodium bicarbonate, and 1 mM EDTA). The mixture was incubated at room temperature for 1 minute.

The sample was centrifuged at 7,200×g for one minute and the supernatant was aspirated and discarded. 300 microliters of cell lysis solution (typically 2% sodium dodecyl sulfate, 68 mM sodium citrate, 132 mM citric acid, 10 mM EDTA) was added and mixed by pipetor cycling. On hundred microliters of Protein Precipitation Solution (typically 10 M ammonium acetate) were added and the samples were vortexed for 20 seconds and centrifuged at 7,200×g for two minutes.

The supernatants were transferred into 300 microliters of isopropanol and the samples gently inverted 50 times and centrifuged at 7,200×g for two minutes. The isopropanol was decanted and the tubes allowed to dry for 2 minutes. Three hundred microliters of 70% ethanol were added, the tubes were inverted 10 times to wash each DNA pellet, and the samples were then centrifuged at 7,200×g for two minutes. The ethanol was decanted and the tubes allowed to dry over a paper towel for 15 minutes. One hundred microliters of DNA hydration solution (typically 10 mM Tris.HCl pH 8.0, 1 mM EDTA) was added to each sample and the DNA samples were allowed to dissolve overnight at room temperature.

Clinical laboratory Factor V Leiden DNA Test Protocol

DNA was extracted using the Gentra Capture column system as described above. The DNA was amplified by PCR reaction using the primers 5' GAG AGA CAT CGC CTC TGG GCT A 3' (SEQ ID NO:3) and 5' TGT TAT CAC ACT GGT GCT AA 3' (SEQ ID NO:4). Detection of mutant and wild type sequences was by chemiluminescence using enzyme labeled probes with the sequences 5' TGG ACA GGC GAG GAA TAC 3' (SEQ ID NO:5) for wild type and 5' TGG ACA GGC AAG GAA TAC 3' (SEQ ID NO:6) for the mutant FV genome.

Fifty microliter PCR reactions were run according to the standard protocol. The reaction mixture consisted of 32.5 μl deionized water, 5 μl 10× buffer (500 mM KCl, 100 mM Tris-HCl, pH 9.0, and 1% Triton X-100), 4 μl of 10 mM dNTP's, 2 μl 25 mM $MgCl_2$, 2 μl of each 20 μM primer, SEQ ID NO:3 and SEQ ID NO:4, and 5 μl (2.5 units) of Taq. PCR cycling conditions were: 35 cycles of 90° C. for 30 seconds, 55° C. for 30 seconds and 72° C. for 30 seconds followed by 1 hold at 72° C. for 10 minutes and 6° C. final.

FV wild type and mutant alleles were detected by hybridization with alkaline phosphatase labeled wild type and mutant probes followed by incubation with the Tropix chemiluminescent CSPD® (disodium 3-(4-methoxyspiro{1, 2-dioxetane-3,2'-(5'-chloro)tricyclo[$3.3.1.1^{3,7}$]decan}-4-yl) phenyl phosphate)(Tropix, Bedford, Mass. 01730) Briefly, 1 μl of PCR product was spotted onto Oncor/Intergen Sure Blot™ membrane. The same spotting pattern was used for the two membranes, one for wild type and one for mutant allele detection. After 5 minutes of DNA denaturation in 0.2 M NaOH, the membranes were incubated at 53° C. for 30 minutes in Tropix blocking buffer(2 g I-Block (Tropix), 100 ml 10×PBS[2.2 g $NaH_2PO_4$, 11.9 g $Na_2HPO_4$, 83 g NaCl dissolved in 1 liter of deionized water], 50 ml of 10% Sodium dodecyl sulfate solution in 1 liter of deionized water). This was followed by incubation at 53° C. for 30 minutes for one membrane with the wild type and one membrane with mutant probe in Tropix buffer followed by two 5 minute washes with Tropix washing buffer(100 ml 10×PBS, 50 ml 10% sodium dodecyl sulfate in 1 liter of deionized water) at 53° C. The membrane was then washed 2× with Tropix AMPPD buffer (2 ml of 0.5M $MgCl_2$, 10 ml diethanolamine dissolved in deionized water, pH 10) and was incubated 20 minutes with CSPD substrate (50 μl CSPD solution in 10 ml AMPPD buffer) wrapped in Saran Wrap™ with a photographic film held adjacent to the Saran Wrap™ at the surface of the membrane. Development of the film demonstrated a spot where labeled probe was bound to the membrane.

One membrane was probed with the wild type probe and the other was probed with the mutant probe.

Research Laboratory FV Leiden Test Protocol

The protocol described herein is a commonly used clinical laboratory protocol and is representative of many FV DNA testing protocols currently in use and known in the art. It was used in the research laboratory because the DNA extraction protocol requires dilution followed by separation of the cellular or bound DNA complex from its liquid matrix as one of the first steps. Products not demonstrating avid nucleic acid binding would lose their DNA in this step. DNA was extracted using the Gentra Puregene method as described above. The DNA was amplified by PCR reaction using the primers 5' GAG AGA CAT CGC CTC TGG GCT A 3' (SEQ ID NO:3) and 5' TGT TAT CAC ACT GGT GCT AA 3' (SEQ ID NO:4). Detection of the DNA segment of the expected size was by 2% agarose gel electrophoresis followed by ethidium bromide staining of the DNA bands and visualization under ultraviolet light.

Fifty microliter PCR reactions were run according to standard protocol. The reaction mixture was as described above in the clinical laboratory FV Leiden protocol. Ten μl of PCR product were mixed with 10 μl of 2× loading buffer (typically 4% Ficoll 400, 0.02 M EDTA (pH 8.0), 0.2% SDS, 0.05% bromophenol blue, 0.05% xylene cyanol) and electrophoresed on 2% low melting point agarose at 100 mA for 30 minutes. 200 ng of a 100 bp ladder was run in an adjacent lane of the gel to provide molecular weight markers. To visualize the DNA bands the gel slab was incubated for 15 minutes in an 0.5 μg/ml ethidium bromide solution and viewed with UV light at 230 nm. The gel was photographed with either a Polaroid camera or a digital camera and the bands between specimens and between runs were compared visually.

The Results of the experiments presented in this example are now described.

The data disclosed herein demonstrate that nucleic acid can be incubated with a nylon microparticle and in that form may be separated from its liquid suspension by centrifugation and carried through the DNA extraction procedure and subsequent procedures of a genetic test resulting in detection of that DNA in the genetic test. This was demonstrated by preparing a reference DNA-binding agent composition comprising FV plasmid DNA and nylon microparticles and subjecting said composition to genetic testing.

Following preparation of the FV DNA-nylon microparticle composition, DNA was extracted from the product at intervals (Capture DNA Isolation Kit) and tested for detection of the FV DNA segment in a clinical laboratory PCR based FV assay. One open vial containing 5 ml of the product was tested over a 242 day period with 300 μl aliquots removed for each testing episode. FIG. 2 depicts the dot blots obtained over the time period of the testing. Visual comparison of the dots intensity with that of the intensity of dots of unidentified patient samples on the films indicates that the level of DNA obtained did not decrease during the period of the testing and is comparable to that of routine patient samples.

Briefly, the dot blot was produced using a clinical laboratory PCR based FV assay aimed at the detection of wild type and mutant FV DNA segments in blood samples following a DNA extraction and amplification procedure all of which are well-known in the art. The regions indicated by the arrows labeled "Ctrl" are the areas dotted with PCR product of extracted FV plasmid DNA-nylon nucleic acid reference standard. The other dots are those amplified from testing DNA extracted from unidentified blood samples and are included for comparison purposes. The upper rows of dots represent signal from the wild type gene and the lower rows with dots having the same number represent the corresponding signal from probing of the sample with a mutant probe. The dot blot test for detection of specific DNA sequences was performed as follows: DNA was extracted from control samples and patient samples and amplified by PCR using protocols standard in the clinical laboratory. One μl of PCR product was placed on a nitrocellulose membrane, denatured, and then reacted with alkaline phosphatase enzyme labeled probe at 53° C. Two separate membrane dots were made for each sample. One dot was incubated with labeled wild type probe and one with a probe containing the FV mutant sequence. The membranes were then incubated with detection reagent that produced chemiluminescence in the presence of alkaline phosphatase. A photographic film was placed over the sample to detect light emitted by chemiluminescence. If the sequence on the probe exactly matched the sequence of the patient or control then the enzyme labeled probe was retained and a chemiluminescence was produced when the detection reagent was added. If the sequences did not match exactly, then the labeled probe did not bind at 53° C. and no signal was obtained.

In FIGS. 2A-2G, the area designated by the arrow is the signal from extracted and amplified wild type FV plasmid-Nylon microparticle nucleic acid reference standard. The other dots are those from testing unidentified blood samples and are included for comparison purposes. The upper rows of dots represent signal from the wild type gene and the lower rows with dots having the same number represent the corresponding signal from probing of the sample with a mutant probe.

The DNA extraction, amplification and dot blot test depicted in FIG. 2A was performed 9 days after generation of the FV DNA-nylon nucleic acid reference standard. The dot blot test depicted in FIG. 2B was performed 26 days after generation of nucleic acid reference standard. The dot blot test depicted in FIG. 2C was performed 70 days after generation of the nucleic acid reference standard. The dot blot test depicted in FIG. 2D was performed 103 days after generation of the nucleic acid reference standard. The dot blot test depicted in FIG. 2E was performed 151 days after generation of the nucleic acid reference standard. The dot blot test depicted in FIG. 2F was performed 159 days after generation of the nucleic acid reference standard. The dot blot test depicted in FIG. 2C was performed 242 days after generation of the nucleic acid reference standard.

These results demonstrated the stability of the control product over a period of 242 days and demonstrated that the dot blot intensity of the reference was comparable to that seen for patient samples. The results also demonstrate that the control with wild type sequence was correctly detected by the wild type probe and not detected by the mutant probe in all instances.

One skilled in the art would appreciated, based upon the disclosure provided herein, that a product mimicking a mammalian cell in reliably yielding DNA on extraction and consistently providing a result in a genetic test has value as a reference material for that test. This is especially so where the product is stable and has a long shelf life.

Figure 1:
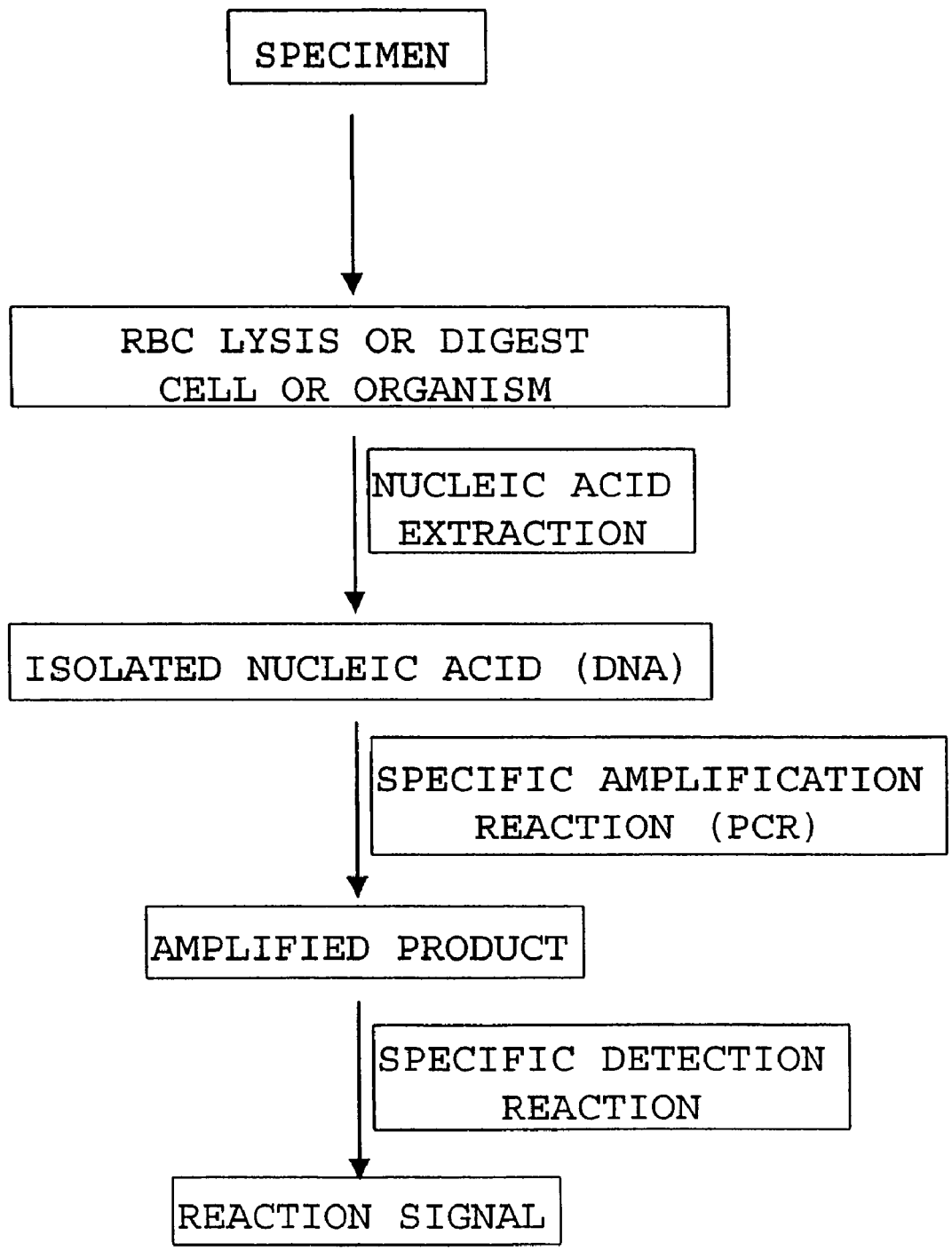
FIG. 1 is a diagram depicting typical steps in a nucleic acid assay.

In a variation of the experiment, product was added to a PCR reaction without subjecting the product to DNA extraction. No test result was obtained from the research FV DNA test. The nucleic acid extraction is an important part of a genetic test. If this part of the test is not performed properly, an erroneous result may result. Therefore, the data disclosed herein demonstrate that the product mimics a cell or virus particle and has important value as a reference material to evaluate the DNA extraction step of a genetic test (FIG. 1). Indeed, the research FV DNA test was used for this experiment since it included an RBC lysis step followed by concentration of DNA containing cells or microparticulates in the extraction protocol. The DNA binding affinity measured by the ability of the bound reference DNA to be carried through the RBC step was assessed using this protocol. The data disclosed herein demonstrate that the product, also referred to herein as a nucleic acid reference standard and as a nucleic acid reference standard, which terms are used interchangeably herein, withstood the extraction step and mimicked the extraction of nucleic acid from a cell in that, inter alia, nucleic acid was not detected absent an extraction step.

The data disclosed herein further demonstrate that an amount of plasmid nucleic acid equivalent to that usually extracted was added directly to the extraction protocol. There was no DNA detected using in either the clinical FV DNA testing protocol or the research protocol where extracted plasmid was used without being bound with the binding agent.

Without wishing to be bound by any particular theory, the data disclosed herein demonstrate that extracted DNA from the product consistently gave positive signal indicating successful extraction and detection. Further, the data disclosed herein demonstrate that direct PCR on DNA adsorbed to microparticles yielded negative results indicating that the extraction step was necessary for DNA analysis similar to the requirement that DNA be extracted from a biological sample before it can be detected by standard assays. In addition, the data demonstrate that extracted plasmid yielded negative results in the PCR analysis which demonstrates that the microparticulate adsorbed nucleic acid reference standard, i.e., the nucleic acid reference standard, was necessary to stabilize and carry the DNA through the RBC lysis, or some other, step of the test. Moreover, the data disclosed herein demonstrate that the dot blot intensity remained unchanged throughout the 242 day period of the study indicating the product had significant stability in aqueous suspension.

Nylon (caprolactam) microparticles, the product of grinding of the Nylon, was incubated with DNA in an experiment as described above and also in variations on that protocol. The data disclosed herein demonstrate that DNA was not bound to those microparticles obtained by grinding in amounts detectable or measurable by the techniques used above. Without wishing to be bound by any particular theory, it may be that the microparticles of ground Nylon did not have sufficient reactive surface area to bind a detectable quantity of DNA.

These data demonstrate the use of nylon microparticles to bind and stabilize DNA to produce a nucleic acid reference standard useful as a quality control in nucleic acid assays. That is, DNA adsorbed to a reactive nylon microparticle was released for testing in clinical DNA extraction protocols. The utility of the novel nucleic acid reference standard was demonstrated as a reference to validate the extraction protocol and the DNA detection steps in various standard clinical assays.

EXAMPLE 2

Linearized and Non-linearized Plasmid DNA in Reference DNA Compositions

The experiments presented in this example may be summarized as follows.

The data disclosed herein describe the preparation of nucleic acid reference standard nucleic acid/binding agent compositions comprising linearized and non-linearized nucleic acid and the use of these compositions in genetic testing.

The Materials and Methods used in the experiments presented in this example are now described.

Preparation of a Nucleic Acid Reference Standard
(Reference DNA-vector) Composition FV plasmid DNA was diluted to 235 ng/ml, and nylon microparticles were prepared in a concentration of 40 mg/ml in a 0.2 M sodium acetate, pH 5.2 solution. Seventy-five microliters of the FV plasmid solution was added to 800 µl of the nylon microparticle suspension. After vortex mixing, the suspension was diluted to 10 ml with a storage solution (3 ml glycerol, 28.5 ml 0.026 M EDTA, pH 8.7). The mixture was vortex mixed and stored at 4° C.

The Results of the experiments presented in this example are now described.

The nucleic acid was extracted from the nucleic acid reference standard and was assessed for the presence or absence of the FV DNA segment in the research PCR based FV assay.

FIG. 3 is an image of a 2% agarose gel with ethidium bromide stained FV DNA extracted and amplified from nucleic acid reference standards of the invention. The amplicons were produced by a research PCR based FV assay aimed at detection of an FV DNA segment in samples following a DNA extraction process. The FV DNA in these samples is a reference FV DNA segment cloned into a plasmid. The DNA amplicons shown in the figure demonstrate embodiments of the invention wherein a nucleic acid reference standards with extractable DNA are generated. Nucleic acid reference standards were produced with DNA bound to microparticles of high surface area nylon, of high surface area nylon at high pH, of amine modified polystyrene and of liposomes. The figure also demonstrates the production of a nucleic acid reference standard with extractable linearized and circular reference FV plasmid DNA bound to microparticles of high surface area nylon and to amine modified polystyrene.

In the gel, which was 2% agarose, 2µ of extracted DNA was added to each PCR run and 10 microliters of PCR product was added to each lane of the gel. DNA samples detected on the gel are amplified products of DNA extracts from sources described below. The gel was electrophoresed at 70 mA for 30 minutes. The gel was stained with 0.5 microgram/ml ethidium bromide solution and photographed while illuminated with 230 nM ultraviolet light.

FIG. 3 (lanes 4 and 5) depicts electrophoresis gel signals representing detection of the 221 base pair FV DNA segment from non-linearized N61A and linearized N61B plasmid samples.

These data demonstrate the use of Nylon microparticles to bind and stabilize linearized and non-linearized DNA. Both DNA elements adsorbed to Nylon microparticles were released using a routine DNA extraction protocol. The data disclosed herein demonstrate for the first time, use of a Nylon microparticle-based nucleic acid reference standard as a reference to validate the extraction protocol and the DNA detection steps for both linear and non-linear nucleic acid in a clinical genetic assay.

The data also demonstrate comparable performance from the binding of linearized plasmid and non-linearized plasmid to nylon based microparticles.

EXAMPLE 3

Amine Modified Polystyrene Microparticles as the Vector in Reference DNA Compositions The experiments presented in this example may be summarized as follows.

The data disclosed herein describe the preparation of nucleic acid reference standard (nucleic acid/binding agent) compositions, i.e., nucleic acid reference standard, comprising amine modified polystyrene as the binding agent and the use of these compositions in genetic testing.

The Materials and Methods used in the experiments presented in this example are now described.

Preparation of Reference DNA-vector Composition

Factor V (FV) plasmid DNA prepared as described previously elsewhere herein, was diluted to 23.5 ng/ml, salmon sperm DNA was prepared in a solution of 218 µg/ml. One and a half milliliters of the FV plasmid DNA solution was incubated with 50 mg of Polybead Amino 0.74 micron latex microspheres (Polysciences, Inc., Warrington, Pa.) for 5 minutes at room temperature. The sample was centrifuged and the supernatant was discarded. One milliliter of the salmon sperm solution was added, the sample was vortexed and incubated at room temperature for 2 minutes, centrifuged 2 minutes at 7200×g, and the supernatant was discarded. Another 1 ml of salmon sperm DNA solution was added. This suspension was vortex mixed and stored at 4° C.

Linearized and non-linearized FV reference DNA was incubated with amine modified polystyrene in another set of preparations. Briefly, solutions of linearized and non-linearized FV plasmid DNA were diluted to 235 ng/ml, and Polybead Amino 0.74 micron latex microspheres were obtained in a suspension of 2.7% solid. Two samples were made by adding 75 µl of FV plasmid solution to 800 µl of the amine modified polystyrene microparticle suspensions. After vortex mixing, the suspensions were diluted to 10 ml with a storage solution (3 ml glycerol, 28.5 ml 0.026 M EDTA, pH 8.7). The mixture was vortexed and stored at 4° C.

The Results of the experiments presented in this example are now described.

The DNA was extracted from the nucleic acid reference standard and assessed for detection of the FV DNA segment in the research PCR based FV assay described previously elsewhere herein. FIG. 4 (lane 6) depicts electrophoresis gel signal representing detection of the 221 base pair FV DNA segment. FIG. 3 (lanes 6 and lane 7) shows electrophoresis gel signals representing detection of the non-linearized (Polu61A) and linearized plasmid (Polu61B) DNA, respectively.

These data demonstrate the use of amine functionalized polystyrene microparticles to bind and stabilize DNA. DNA adsorbed to amine functionalized polystyrene was released for testing in clinical DNA extraction protocols. Utility is demonstrated for the product as a reference to validate the extraction protocol and the DNA detection steps in a clinical assay. The data also demonstrate comparable performance from the binding of linearized plasmid and non-linearized plasmid.

EXAMPLE 4

Liposome as the Vector in Reference DNA-vector Compositions

The experiments presented in this example may be summarized as follows.

The data disclosed herein describe the preparation of reference DNA-vector compositions comprising liposomes as the vector and the use of these compositions in genetic testing.

The Materials and Methods used in the experiments presented in this example are now described.

Preparation of Nucleic Acid Reference Standard (Nucleic Acid/Binding Agent) Composition Comprising Liposomes FV plasmid DNA was diluted to 23.5 ng/ml. 200 µl of a 5 mg/ml salmon sperm DNA solution was added to 5 ml of the FV plasmid solution making a final solution of 200 µg/ml total DNA. Liposomes were prepared under nitrogen atmosphere by mixing, in a 2 ml glass tube, 35 µl of 1,2-dioleoyl-3-trimethylammonium propane (DOTAP) (20 mg/ml in chloroform) with 74 µl of dipalmitoyl lecithin (10 mg/ml in chloroform) and evaporating the chloroform under a nitrogen stream while swirling the tube. 1 ml of deionized water was added to the dried lipid under nitrogen and the mixture was sonicated for 2 minutes to produce liposomes.

Eight-hundred microliters of the FV and salmon sperm DNA solution and 0.2 ml of deionized water was added, under nitrogen, with mild mixing and the was suspension incubated at room temperature for 12 hours. The suspension had visibly cleared after 12 hours and was stored in a capped glass vial at 4° C.

The Results of the experiments presented in this example are now described.

The DNA was extracted from the nucleic acid reference standard after 5 months of 4° C. storage and tested for detection of the FV DNA segment in the research PCR based FV assay. FIG. 3 (lane 9) depicts electrophoresis gel signals representing detection of the 221 base pair FV DNA segment from the test.

These data demonstrate the use of liposomes to bind and stabilize DNA. DNA incubated with a liposome was released for testing in a routine DNA extraction protocol. The experiment demonstrates use of the product as a reference to validate the extraction protocol and the DNA detection steps in a clinical genetic assay.

EXAMPLE 5

Nucleic Acid-Binding Agent (Nucleic Acid Reference Standard) Compositions in the Presence of Chaotropic Salts The experiments presented in this example may be summarized as follows.

The data disclosed herein demonstrate the preparation of novel compositions comprising a target nucleic acid of interest and a binding agent in the presence of Chaotropic salts and the use of these compositions in a clinical genetic assay.

The Materials and Methods used in the experiments presented in this example are now described.

Preparation of Reference DNA-Vector Composition

FV plasmid DNA was diluted to 235 ng/ml, and Nylon microparticles were prepared in a concentration of 38 mg/ml in deionized water. Twenty-five microliters the FV plasmid solution was added to 266 µl of the nylon microparticle suspension and the suspension was diluted to 3 ml with 6M sodium iodide solution. After vortex mixing the suspension was stored at 4° C.

The Results of the experiments presented in this example are now described.

The DNA was extracted from the nucleic acid reference standard and assessed for detection of the FV DNA segment in the research PCR based FV assay described previously elsewhere herein. FIG. 5 (lane 2) depicts the electrophoresis gel signal demonstrating detection of the 221 base pair FV DNA amplicon from the test.

These data demonstrate the use of nylon microparticles in combination with chaotropic salt solution to bind and stabilize a target nucleic acid of interest. More specifically, DNA associated with/adsorbed onto nylon microparticles in a chaotropic sodium iodide salt solution were released for detection using in a routine DNA extraction protocol commonly used in the art. The experiment demonstrates use of a nylon based nucleic acid reference standard in a chaotropic salt solution as a quality nucleic acid reference standard to assess and validate the extraction protocol and the DNA detection steps for both linear and non-linear DNA in a clinical genetic assay.

EXAMPLE 6

Nucleic Acid Reference Standard (Nucleic Acid-binding Agent) Compositions in the Presence of Alcohol The experiments presented in this example may be summarized as follows.

The data disclosed herein describe the preparation of novel compositions comprising a nucleic acid reference standard comprising target nucleic acid of interest and a binding agent in the presence of alcohol and the use of these nucleic acid reference standard compositions in a clinical genetic assay.

The Materials and Methods used in the experiments presented in this example are now described.

Preparation of Reference DNA-Vector Compositions

FV plasmid DNA prepared as described previously elsewhere herein was diluted to 235 ng/ml. Nylon microparticles prepared as described previously elsewhere herein were adjusted to a concentration of 38 mg/ml in deionized water. Twenty-five microliters of the FV plasmid solution was added to 266 µl of the Nylon microparticle suspension and the mixture was diluted to 3 ml with 70% ethanol. After vortex mixing the suspension was stored at 4° C.

The Results of the experiments presented in this example are now described.

DNA was extracted from the nucleic acid reference standard and was tested for detection of the FV DNA segment in the research PCR based FV assay as described previously elsewhere herein. FIG. 5 (lane 3) shows detection of the 221 base pair amplicon using electrophoresis/ethidium bromide analysis thereby demonstrating detection of the FV DNA segment using the nucleic acid reference standard.

These data demonstrate the use of nylon microparticles in combination with an alcohol solution to bind and stabilize DNA. DNA adsorbed to Nylon microparticles in an alcohol solution were released for testing in a routine DNA extraction protocol commonly performed in the art. The data disclosed herein demonstrate use of a nylon based nucleic acid reference standard in an alcohol solution as a reference quality control standard useful to validate the extraction protocol and the DNA detection steps for both linear and non-linear DNA in a clinical genetic assay.

EXAMPLE 7

Silica Gel Microparticles as the Vector in Reference DNA-Vector Compositions

The experiments presented in this example may be summarized as follows.

The data disclosed herein describe the preparation of nucleic acid reference standard (nucleic acid-binding agent) compositions comprising silica gel microparticles as the binding agent in the presence of chaotropic salts and the use of these compositions in a clinical genetic assay.

The Materials and Methods used in the experiments presented in this example are now described.

DNA Extraction Using QIAmp® DNA Blood Mini Kit

DNA extraction by the QIAmp® DNA Blood Mini Kit (Qiagen Inc., Chatsworth, Calif.) was performed according to manufacturer's instructions. Briefly, 20 µl of proteinase K solution was added to a 1.5 ml tube followed by 200 µl of DNA/microparticulate suspension, i.e., the nucleic acid reference standard (nucleic acid-binding agent). Two-hundred microliters of buffer (typically 50 mM Tris-HCl (pH 7.5), 5 mM $CaCl_2$) was mixed in by pulse vortexing and the mixture incubated at 56° C. for 10 minutes. After pulse centrifugation, 200 µl of 100% ethanol was added to the mixture which was then vortexed and added to a 1 ml spin column (typically, but not necessarily, using a silica/silica fiber filter). DNA was separated onto the filter of the spin column by centrifugation at 7200×g for 2 minutes. 500 µl of wash buffer (typically 2 M guanidium thiocyanate, 25 mM Tris-HCl, pH 7.5, 30% ethanol) was added to the spin column followed by centrifugation at 7200×g for 1 minute. 500 µl of second wash solution (typically 70% ethanol) was added to the spin column followed by centrifugation at 7200×g for 3 minutes. The DNA was eluted from the column with 200µl of buffer (typically 10 mM Tris, pH 8.5).

DNA Extraction by the Phenol/Chloroform/Isoamyl Alcohol Method

Phenol/chloroform/isoamyl alcohol DNA extraction protocol was performed according to established protocols. More specifically, 20 µl of proteinase K solution (typically 1 µg/µl) was added to a 1.5 ml tube followed by 200 µl of DNA/microparticulate suspension. 200 µl of buffer (typically 50 mM Tris-HCl, pH 7.5, 5 mM $CaCl_2$) was mixed in by pulse vortexing and the mixture was incubated at 56° C. for 10 minutes. Two-hundred microliters of phenol/chloroform/isoamyl alcohol solution (25:24:1 v/v/v) were added to the mixture and vortexed for 30 seconds followed by centrifugation for two minutes. The aqueous (top) layer was removed and placed in a clean tube and DNA was precipitated with 100 µl of cold ethanol followed by incubation at −20° C. for 15 minutes. The sample was centrifuged at 7200×g for 3 minutes and the alcohol was decanted. The DNA pellet was washed with 1 ml of room temperature 70% ethanol, centrifuged for 2 minutes at 7200×g and air dried for 15 minutes. The pellet was then dissolved in 100 µl of 1×TE buffer, pH 7.5 by incubating at 65° C. for 5 minutes.

Preparation of Reference DNA-Vector Compositions

FV plasmid DNA was diluted to 235 ng/ml. One-hundred microliters of the FV plasmid solution was added to 50 mg silica gel (70-230 mesh 60 A pore size; Sigma Chemical Co., St. Louis, Mo.) and the suspension diluted to 10 ml with 100% ethanol. After vortex mixing the suspension was stored at 4° C.

In a companion experiment, 1 ml of 260 µg/ml salmon sperm DNA in DI water was added to 50 mg Silica Gel (70-230 mesh 60 A pore size) followed by 100 µl of the FV plasmid DNA solution and the suspension was diluted to 10 ml with 100% ethanol. After vortex mixing the suspension was stored at 4° C.

The Results of the experiments presented in this example are now described.

DNA was extracted, using the Gentra Puregene method, from the nucleic acid reference standard (nucleic acid-binding agent) and the ability of the target nucleic acid sequence, e.g., the FV DNA segment, to be detected was assessed using a research PCR based FV assay commonly used and standard in the art. FIG. 5 (lane 6 and lane 7) shows the electrophoresis gel signal demonstrating detection of the 221 base pair FV DNA amplicon from the tests using FV plasmid DNA+salmon sperm DNA and FV plasmid DNA only, respectively.

In a companion experiment, the DNA was extracted from the reference using a QIAgen spin column method and otherwise tested in the PCR based research FV assay described previously elsewhere herein. FIG. 5 (lane 8 and lane 9) depicts the electrophoresis gel signal demonstrating detection of the 221 base pair FV DNA segment from the tests for FV plasmid DNA+Salmon Sperm DNA and FV plasmid DNA only, respectively.

In yet another assay, the DNA was extracted from the nucleic acid reference standard (nucleic acid-binding agent) using the phenol/chloroform method and otherwise tested in the PCR based research FV assay as described previously elsewhere herein. FIG. 5 (lane 10 and lane 11) depicts the electrophoresis gel signal demonstrating detection of the 221 base pair FV DNA segment from the tests for FV plasmid DNA+Salmon Sperm DNA and FV plasmid DNA only, respectively.

The data disclosed herein demonstrate the use of silica gel microparticles as a binding agent in combination with and alcohol solution to bind and stabilize a target nucleic acid. That is, DNA adsorbed to silica gel microparticles in an alcohol solution were released for testing in a routine DNA extraction protocol. The data demonstrate use of a silica gel based product in an alcohol solution as a binding agent which when bound with a target nucleic acid encoding a sequence of interest, serves as a nucleic acid reference standard to validate the extraction and detection steps of the protocol. Data demonstrating that similar signal was obtained from the genetic test when extracting the DNA sample using three different extraction methods demonstrates a broad utility and applicability of this nucleic acid reference standard to validate DNA extraction and testing and thus serve as a quality control standard in assays where nucleic acid extraction is performed.

EXAMPLE 8

Aminopropyl Glass as Binding Agent in Nucleic Acid Reference Standard Compositions The experiments presented in this example may be summarized as follows.

The data disclosed herein describe the preparation of novel nucleic acid reference standards (i.e., nucleic acid-binding agent compositions) comprising aminopropyl glass as the binding agent and the use of these compositions in a clinical genetic assay.

The Materials and Methods used in the experiments presented in this example are now described.

Preparation of Nucleic Acid Reference Standard (Nucleic Acid-binding Agent Compositions)

Twenty-five microliters of FV plasmid solution (235 ng/ml) was added to 50 mg aminopropyl glass (Sigma, St. Louis, Mo.) and the suspension was diluted to 3 ml with 70% ethanol. After vortex mixing the suspension was stored at 4° C.

In a companion experiment, FV plasmid was incubated with aminopropyl glass in the presence of chaotropic salt. That is, 25 µl of 25 ng/ml FV plasmid solution was added to 50 mg aminopropyl glass and the suspension was diluted to 3 ml using a 6 M guanidium HCl solution. After vortex mixing the suspension was stored at 4° C.

The Results of the experiments presented in this example are now described.

The DNA was extracted from the nucleic acid reference standard (i.e., nucleic acid-binding agent composition) in 70% ethanol and tested for detection of the FV DNA segment using the research PCR based FV assay described previously elsewhere herein. FIG. 5 (lane 4) depicts the electrophoresis gel signal demonstrating detection of the 221 base pair FV DNA segment from the test.

The data disclosed herein demonstrate the use of aminopropyl glass microparticles in combination with chaotropic salt and/or alcohol solution to bind and stabilize DNA. More specifically, DNA adsorbed to Aminopropyl glass microparticles in an alcohol solution was released for testing in a routine DNA extraction protocol. The experiment demonstrates use of an aminopropyl glass based product in an alcohol solution to produce a nucleic acid reference standard useful to validate the extraction protocol and the DNA detection steps for both linear and non-linear DNA in an assay comprising DNA extraction and/or detection.

In a companion experiment, DNA was extracted from the nucleic acid reference standard in 6 M guanidine:HCl solution and tested for detection of the FV DNA segment in the research PCR based FV assay. FIG. 5 (lane 5) depicts the electrophoresis gel signal representing detection of the 221 base pair FV DNA segment from the test.

The data disclosed herein demonstrate the use of aminopropyl glass microparticles in combination with a chaotropic salt, e.g., guanidium HCl, solution to bind and stabilize DNA. DNA adsorbed with aminopropyl glass microparticles in a chaotropic salt guanidium HCl solution were released for testing in a routine DNA extraction protocol. The data disclosed herein demonstrate the successful use of an aminopropyl glass based product in a chaotropic salt guanidium HCl solution as a reference to validate a nucleic acid extraction protocol and the nucleic acid detection steps in a clinical genetic assay.

EXAMPLE 9

Fumed Silica as Binding Agent in Nucleic Acid Reference Standard Compositions The experiments presented in this example may be summarized as follows.

The data disclosed herein describe the preparation of novel nucleic acid reference standards (i.e., nucleic acid-binding agent compositions) comprising fumed silica as the binding agent in an isopropanol solvent mixture and the use of these compositions in a clinical genetic assay.

The Materials and Methods used in the experiments presented in this example are now described.

Preparation of Nucleic Acid Reference Standard (Nucleic Acid-binding Agent Compositions)

Solutions used in the preparation of the nucleic acid reference standard are as follows:

DNA precipitation solution 1 (2.5 ml of 3.5 M sodium acetate, pH 5.2, 7.5 ml concentrated acetic acid, 20 ml of isopropanol).

DNA precipitation solution 2 (2.5 ml of 3.5 M sodium acetate, pH 5.2, 7.5 ml concentrated acetic acid, 6.7 ml glycerol 13.3 ml of isopropanol).

Chitosan Solution (535 mg high molecular weight chitosan dissolved with heating in 1 ml concentrated acetic acid and 39 ml of deionized water).

A nucleic acid reference standard was prepared by adding 167 mg of fumed silica microparticles (CAB-O-SIL® EH-5, Cabot Corporation, Tuscola, Ill.) (autoclaved) to 83.3 µl of 495 µg/ml FV plasmid DNA and the volume adjusted to 30 ml with DNA precipitation solution 1.

The DNA was extracted from the nucleic acid reference standard (i.e., nucleic acid-binding agent composition) in isopropanol:acetate mixture and tested for detection of the FV DNA segment using the research PCR based FV assay described previously elsewhere herein. FIG. 6 (lane 2) depicts the electrophoresis gel signal demonstrating detection of the 221 base pair FV DNA segment from the test. DNA from the RBC lysis solution was precipitated and recovered and reconstituted in the same volume as the extract tested in lane 2. FIG. 6 lane 8 depicts the DNA from the extraction that was carried into the RBC lysis supernatant.

The data disclosed herein demonstrate the use of fumed silica microparticles in combination with alcohol:acetate solution to bind and stabilize DNA. Comparison of the bands in lane 2 and lane 8 demonstrate that a significant quantity of reference DNA adsorbed to fumed silica microparticles in an alcohol solution was carried through the RBC lysis step and released in the cell lysis step for testing in a routine DNA extraction protocol. The experiment demonstrates use of an fumed silica based product in an alcohol solution to produce a nucleic acid reference standard useful to validate the extraction protocol and the DNA detection steps in an assay comprising DNA extraction and/or detection.

In a companion experiment 167 mg of fumed silica microparticles (CAB-O-SIL® EH-5) (autoclaved) was added to 83.3 µl of 495 µg/ml FV plasmid DNA and 30 µl of 200 µg/ml salmon sperm DNA, and the volume adjusted to 30 ml with DNA precipitation solution 1.

The DNA was extracted from the nucleic acid reference standard (i.e., nucleic acid-binding agent composition) in isopropanol:acetate mixture and was tested for detection of the FV DNA segment using the research PCR based FV assay described previously elsewhere herein. FIG. 6 (lane 3) depicts the electrophoresis gel signal demonstrating detection of the 221 base pair FV DNA segment from the test. DNA from the RBC lysis solution was precipitated and recovered and reconstituted in the same volume as the extract tested in lane 3. FIG. 6 lane 9 depicts the DNA from the extraction that was carried into the RBC lysis supernatant.

The data disclosed herein demonstrate the use of fumed silica microparticles in combination with alcohol:acetate solution to bind and stabilize reference DNA accompanied by salmon sperm "filler" DNA. Comparison of the bands in lane 3 and lane 9 demonstrates that a significant quantity of DNA adsorbed to fumed silica microparticles in an alcohol solution was carried through the RBC lysis step and released in the cell lysis step for testing in a routine DNA extraction protocol. The experiment demonstrates use of an fumed silica based product in an alcohol solution to produce a nucleic acid reference standard containing extra DNA that is useful to validate the extraction protocol and the DNA detection steps in an assay comprising DNA extraction and/or detection.

In a companion experiment 16.7 mg of fumed silica microparticles (CAB-O-S IL® EH-5) (autoclaved) was added to 8.3 μl of 495 μg/ml FV plasmid DNA and the volume adjusted to 3.0 ml with DNA precipitation solution 2 which contained glycerol.

The DNA was extracted from the nucleic acid reference standard (i.e., nucleic acid-binding agent composition) in isopropanol:glycerol:acetate mixture and tested for detection of the FV DNA segment using the research PCR based FV assay described previously elsewhere herein. FIG. 6 (lane 5) depicts the electrophoresis gel signal demonstrating detection of the 221 base pair FV DNA segment from the test. DNA from the RBC lysis solution was precipitated and recovered and reconstituted in the same volume as the extract tested in lane 5. FIG. 6 lane 11 depicts the DNA from the extraction that was carried into the RBC lysis supernatant.

The data disclosed herein demonstrate the use of fumed silica microparticles in combination with alcohol:glycerol: acetate solution to bind and stabilize reference DNA. Comparison of the bands in lane 5 and lane 11 demonstrates that a significant quantity of DNA adsorbed to fumed silica microparticles in an alcohol solution was carried through the RBC lysis step and released in the cell lysis step for testing in a routine DNA extraction protocol. The experiment demonstrates use of an fumed silica based product in an alcohol: glycerol:acetate solution to produce a nucleic acid reference standard containing extra DNA that is useful to validate the extraction protocol and the DNA detection steps in an assay comprising DNA extraction and/or detection.

In a companion experiment 16.7 mg of fumed silica microparticles (CAB-O-SIL®) (autoclaved) was added to 25 μl of 235 μg/ml FV plasmid DNA mixed with 50 μl of chitosan solution and the volume adjusted to 3.0 ml with DNA precipitation solution 1.

The DNA was extracted from the nucleic acid reference standard (i.e., nucleic acid-binding agent composition) in isopropanol:acetate mixture and tested for detection of the FV DNA segment using the research PCR based FV assay described previously elsewhere herein. FIG. 6 (lane 6) depicts the electrophoresis gel signal demonstrating detection of the 221 base pair FV DNA segment from the test. DNA from the RBC lysis solution was precipitated and recovered and reconstituted in the same volume as the extract tested in lane 6. FIG. 6 lane 12 depicts the DNA from the extraction that was carried into the RBC lysis supernatant.

The data disclosed herein demonstrate the use of fumed silica microparticles in combination with alcohol solution to bind and stabilize reference DNA complexed with chitosan. Comparison of the bands in lane 6 and lane 12 demonstrates that a significant quantity of DNA adsorbed to fumed silica microparticles in an alcohol solution was carried through the RBC lysis step and released in the cell lysis step for testing in a routine DNA extraction protocol. The experiment demonstrates use of chitosan to complex silica and the mixture bound to fumed silica microparticles in an alcohol:acetate solution to produce a nucleic acid reference standard that is useful to validate the extraction protocol and the DNA detection steps in an assay comprising DNA extraction and/or detection.

In a companion experiment FV plasmid reference DNA (25 μl in 3 ml of deionized water) was added directly into the DNA extraction. The sample was carried through the protocol in exactly the same manner as the reference specimens and tested for detection of the FV DNA segment using the research PCR based FV assay described previously elsewhere herein. FIG. 6 (lane 13) depicts the electrophoresis gel signal demonstrating detection of a small amount of the 221 base pair FV DNA segment from the test. DNA from the RBC lysis solution was precipitated and recovered and reconstituted in the same volume as the extract tested in lane 13. FIG. 6 lane 14 depicts the DNA from the extraction that was carried into the RBC lysis supernatant. This experiment demonstrates that, without the DNA binding agents and solutions of this invention, DNA recovery from the Gentra Puregene DNA extraction is significantly decreased.

EXAMPLE 10

Low Alumina Zeolite as Binding Agent in Nucleic Acid Reference Standard Compositions The experiments presented in this example may be summarized as follows.

The data disclosed herein describe the preparation of novel nucleic acid reference standards (i.e., nucleic acid-binding agent compositions) comprising low alumina zeolite as the binding agent and the use of these compositions in a clinical genetic assay.

The Materials and Methods used in the experiments presented in this example are now described.

Preparation of Nucleic Acid Reference Standard (Nucleic Acid-binding Agent Compositions)

The experiments presented in this example may be summarized as follows.

The data disclosed herein describe the preparation of novel nucleic acid reference standards (i.e., nucleic acid-binding agent compositions) comprising fumed silica as the binding agent in an isopropanol solvent mixture and the use of these compositions in a clinical genetic assay.

The Materials and Methods used in the experiments presented in this example are now described.

Preparation of Nucleic Acid Reference Standard
(Nucleic Acid-binding Agent Compositions)

Solutions used in the preparation of the nucleic acid reference standard are as follows:

DNA precipitation solution 1 (2.5 ml of 3.5M sodium acetate, pH 5.2, 7.5 ml concentrated acetic acid, 20 ml of isopropanol).

A nucleic acid reference standard was prepared by adding 16.7 mg of low alumina zeolite microparticles(CBV 901; Zeolyst™ International, Kansas City, Kans.) (autoclaved) to 8.3 µl of 495 µg/ml FV plasmid DNA and the volume adjusted to 3.0 ml with DNA precipitation solution 1.

The DNA was extracted from the nucleic acid reference standard (i.e., nucleic acid-binding agent composition) in isopropanol:acetate mixture and tested for detection of the FV DNA segment using the research PCR based FV assay described previously elsewhere herein. FIG. 6 (lane 4) depicts the electrophoresis gel signal demonstrating detection of the 221 base pair FV DNA segment from the test. DNA from the RBC lysis solution was precipitated and recovered and reconstituted in the same volume as the extract tested in lane 4. FIG. 6 lane 10 depicts the DNA from the extraction that was carried into the RBC lysis supernatant.

The data disclosed herein demonstrate the use of fumed low alumina zeolite microparticles in combination with alcohol:acetate solution to bind and stabilize DNA. Comparison of the bands in FIG. 6 lane 4 and lane 10 demonstrate that a significant quantity of reference DNA adsorbed to fumed silica microparticles in an alcohol:acetate solution was carried through the RBC lysis step and released in the cell lysis step for testing in a routine DNA extraction protocol. The experiment demonstrates use of a zeolite based product in an alcohol solution to produce a nucleic acid reference standard useful to validate the extraction protocol and the DNA detection steps in an assay comprising DNA extraction and/or detection.

EXAMPLE 11

Measurement of DNA Binding Capacity of Selected Binding Agents

The experiments presented in this example may be summarized as follows.

The data disclosed herein describe the DNA binding capacity of selected microparticles, indicative of their efficacy as a binding agents in a nucleic acid reference standard comprising nucleic acid and binding agent which are useful in nucleic acid assays including, but not limited to, clinical genetic assays.

The Materials and Methods used in the experiments presented in this example are now described.

Determination of DNA Binding Capacity of Solids

DNA stock solution was produced by dissolving salmon sperm DNA to a concentration of 0.260 micrograms per ml. The exact concentration was determined for each use by UV spectroscopic measurement. In a 1.5 ml polypropylene tube, 20 to 100 mg of solid was added and, if in a slurry, the sample was centrifuged and the supernatant discarded. One milliliter aliquots of stock DNA were added, the suspension was vortex mixed, incubated for 5 minutes at room temperature and then centrifuged at 7200×g for 2 minutes. The DNA concentration remaining in the supernatant was measured spectroscopically and the amount of DNA absorbed by the solid was estimated by subtraction. If more than 50% of the supernatant DNA had been absorbed by the solid, then the 1 ml supernatant was discarded and another 1 ml aliquot was added until solid DNA binding saturation is indicated by less than 50% absorption of the DNA added.

The Results of the experiments presented in this example are now described.

The DNA binding capacity was determined for several of the nucleic acid reference standards described previously elsewhere herein and the results are summarized in Table 1. The data disclosed herein demonstrate the high nucleic acid binding capacity of the nylon microparticles generated according to the protocol described above.

TABLE 1

| Material Tested | DNA binding µg DNA/mg solid |
|---|---|
| Nylon microparticles | 9 micrograms DNA/mg solid |
| 3 aminopropyl silica (Sigma) | 0.76 micrograms DNA/mg solid |
| Ground Nylon microparticles (EMS) | 0 micrograms DNA/mg solid |
| Trimethylbenzylammonium derivatized polystyrene (Polysciences) | 1.174 micrograms DNA/mg solid |

EXAMPLE 12

CFTR Exon-containing DNA as the Target Nucleic Acid in a Nucleic Acid Reference Standard (Nucleic Acid-binding Agent Compositions)

The experiments presented in this example may be summarized as follows.

The data disclosed herein describe the preparation of novel nucleic acid reference standards (nucleic acid-binding agent compositions) comprising cystic fibrosis transmembrane conductance regulator (CFTR) DNA as the target nucleic acid in a nucleic acid reference standard comprising the nucleic acid and a binding assay. The data further demonstrate the use of the nucleic acid reference standard in a clinical genetic assay demonstrating the usefulness of such compositions in nucleic acid assays.

The Materials and Methods used in the experiments presented in this example are now described.

Preparation of Nucleic Acid Reference Standard

Plasmid sample containing CFTR exons 10 and 11 was diluted to $62 \times 10^4$ copies per µl and combined with a nylon microparticle suspension prepared according to the methods described previously elsewhere herein. The nylon microparticle suspension contained 40 mg/ml of nylon microparticulates in deionized water. An extractable DNA nucleic acid reference standard was prepared as follows.

Nucleic acid reference standard B1P64-2 (31,000 plasmid copies per µl ): 500 µl plasmid solution ($62 \times 10^4$ copies per μl) was added to 800 μl nylon microparticle suspension. This was diluted to 10 ml with 0.025 M EDTA, pH 8.7 in 10% v/v glycerol and stored at 4° C.

DNA Extraction of Sample

B1P64-2 was treated exactly as a patient whole blood sample when extracted using the Rapid DNA Isolation protocol of the Puregene DNA Isolation Kit (Gentra Systems).

The Results of the experiments presented in this example are now described.

Extracted nucleic acid reference standard DNA was tested by amplification and detection using ethidium bromide stained polyacrylamide electrophoresis where B1P64-2 produced a moderate signal. The sample was also tested at the University of North Carolina using a prototype Roche Linear Array CF-31 assay (Roche Diagnostics Corporation, Indianapolis, Ind.).

Method 1 of Testing the CFTR Nucleic Acid Reference Standard

Two microliters of each DNA sample was amplified using Amplitaq Gold® (Applied Biosystems, Foster City, Calif.) PCR described as follows. JG Primers used for amplification were those used to make the original construct: CFEX10F1—5'AACAGCGCGCGACACAGA3' and CFEX11R1 5'CAAACCGGTACACTGACACCAA3'. A 50 μl PCR reaction was prepared to contain 10 mM Tris-HCl, pH8.3, 50 mM KCl, 200 μM each dNTPs, 0.8 μM each primer and 2.5 U of AmpliTaq Gold. Cycling conditions were 95° C. for 10 minutes, 32 cycles of 94° C. for 30 seconds, 55° C. for 30 seconds, 72° C. for 1:30 minutes. The amplification products were then applied to a 6% polyacrylamide gel, separated by electrophoresis and visualized by staining with 0.5 mg/ml ethidium bromide. Sample B1P64-2 produced a moderate signal on the gel.

Method 2 of Testing the CFTR Nucleic Acid Reference Standard

The data disclosed herein further demonstrate the optimization of microparticles for increased yield of DNA bound thereto. The extracted DNA sample B1P64-2 was tested at the University of North Carolina using a prototype of the Roche Linear Array CF-31 assay (Roche Diagnostics Corporation, Indianapolis, Ind.). In the Linear Array test, the alleles containing selected mutations were PCR amplified with biotin labeled primers provided by the manufacturer. The denatured PCR products were hybridized to a strip containing sequences complementary to mutant and wild type alleles. Amplicons that bound to the strip (i.e. contained the complementary sequences) were bound with labeled streptavidin and detected by enzymatic color generation. Testing detected wild type (wt) sequence for all codons tested for exons 10 and 11 (Table 2, column UNC).

TABLE 2

| Sample | A | |
| --- | --- | --- |
| | B1P64-2 | |
| Laboratory | UNC | MMQCI |
| Type of Test | Roche Linear Array CF-31 assay | DNA sequencing |
| Exon | | |
| 10 | Y | Y |
| 11 | Y | Y |

TABLE 2-continued

| Mutation Site | | |
| --- | --- | --- |
| G480 | wt | wt |
| Q493 | wt | wt |
| ΔI507 | wt | wt |
| ΔF508 | wt | wt |
| V520 | wt | wt |
| 1717-1 | wt | wt |
| G542 | wt | wt |
| S549 | wt | wt |
| G551 | wt | wt |
| R553 | wt | wt |
| A559 | NA | wt |
| R560 | wt | wt |
| Polymorphism | | |
| I506V | Wt | wt |
| I507V | Wt | wt |
| F508C | Wt | wt |

UNC refers to the independent referee laboratory that tested the extracted reference DNA product using the Roche Linear Array CF-31 assay. The MMQCI laboratory refers to the site where the reference DNA product was tested by DNA sequencing. The cystic fibrosis reference DNA product was wild type for the cystic fibrosis sequences in exons 10 and 11.

These results demonstrate the binding of target DNA sequences to a microparticulate to produce a nucleic acid reference standard with extractable DNA. Prior art nucleic acid testing nucleic acid reference standards are commonly extracts of cellular DNA or frozen DNA extracts of patient derived specimens. These products are not useful as reference materials for a process involving nucleic acid extraction since DNA in solution will not be recovered at the end of a DNA extraction process. In contrast, the novel nucleic acid reference standards disclosed herein provide stabilization of the DNA on, and extraction of the DNA from, a microparticulate surface and the generation of the expected result in a standard genetic testing protocol thus demonstrating the value and utility of the product of this invention as a reference material.

These data show that the expected sequence for the disease related codons in exons 10 and 11 were detected by both the DNA sequencing test and by the Linear Array test. These data demonstrate the utility of a bound reference DNA preparation of this invention as a material to validate a clinical laboratory testing protocol, including DNA extraction.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of producing a stable isolated nucleic acid reference standard, said reference standard comprising an isolated target nucleic acid comprising a known sequence wherein said isolated nucleic acid is bound with a microparticulate binding agent, said method comprising contacting said isolated target nucleic acid with said microparticulate binding agent, further wherein said binding agent is produced by a method comprising dissolving nylon in concentrated acid to produce a solution and adding said solution dropwise to water, thereby producing a stable isolated nucleic acid reference standard.

2. The method of claim 1, wherein said nylon is nylon 6/6.

3. The method of claim 1, wherein said dropwise addition is about 2 drops per second.

4. The method of claim 1, wherein said composition is stable under a set of conditions selected from the group consisting of: a) at least nine days at about four degrees Celsius; b) at least twenty-six days at about four degrees Celsius; c) at least seventy days at about four degrees Celsius; and d) at least one hundred three days at about four degrees Celsius.

* * * * *

SEQUENCE LISTING

<160> NUMBER OF SEQ ID NOS: 7

<210> SEQ ID NO 1
<211> LENGTH: 21
<212> TYPE: DNA
<213> ORGANISM: Artificial
<220> FEATURE:
<223> OTHER INFORMATION: Primer MMQCIFVF1

<400> SEQUENCE: 1
cttcggcagt gatggtactg a                                     21

<210> SEQ ID NO 2
<211> LENGTH: 22
<212> TYPE: DNA
<213> ORGANISM: Artificial
<220> FEATURE:
<223> OTHER INFORMATION: Primer MMQCIFVR1

<400> SEQUENCE: 2
tgcaatatta attggttcca gc                                    22

<210> SEQ ID NO 3
<211> LENGTH: 22
<212> TYPE: DNA
<213> ORGANISM: Artificial
<220> FEATURE:
<223> OTHER INFORMATION: PCR primer

<400> SEQUENCE: 3
gagagacatc gcctctgggc ta                                    22

<210> SEQ ID NO 4
<211> LENGTH: 20
<212> TYPE: DNA
<213> ORGANISM: Artificial
<220> FEATURE:
<223> OTHER INFORMATION: PCR primer

<400> SEQUENCE: 4
tgttatcaca ctggtgctaa                                       20

<210> SEQ ID NO 5
<211> LENGTH: 18
<212> TYPE: DNA
<213> ORGANISM: Artificial
<220> FEATURE:
<223> OTHER INFORMATION: PCR primer

<400> SEQUENCE: 5
tggacaggcg aggaatac                                         18

<210> SEQ ID NO 6
<211> LENGTH: 18
<212> TYPE: DNA
<213> ORGANISM: Artificial
<220> FEATURE:
<223> OTHER INFORMATION: PCR primer

<400> SEQUENCE: 6
tggacaggca aggaatac                                         18

<210> SEQ ID NO 7
<211> LENGTH: 780

```
<212> TYPE: DNA
<213> ORGANISM: Homo sapiens

<400> SEQUENCE: 7
aaagagcttt atacttttac cagatggtat ctcactgaac ccccaaacag acctgtaaca      60
tttttaggag ggttattacc catttgataa aaggaagaaa ttaggaaagg ctaatcaact     120
tgctcaacac atccaatacc aacagacctg gaatttgaaa ctaagacaaa atatgttatc     180
acactctaga cttgccttcg gcagtgatgg tactgataaa aatagacaag acaaaaaaaa     240
aaaaagaata aatgttatca cactggtgct aaaaaggact acttgacaat tactgttctc     300
ttgaaggaaa tgccccatta tttagccagg agacctaaca tgttctagcc agaagaaatt     360
ctcagaattt ctgaaaggtt acttcaagga caaatacct gtattccttg cctgtccagg      420
gatctgctct tacagattag aagtagtcct attagcccag aggcgatgtc tctcatgatg     480
tccacgtcac tgtagtatgg tcttgttaag cactgggcat cattttctgt gggttcatca     540
aactctaaga tgttccactt ataagtatag gtttcccctg gttgaactgc tctgatcatg     600
gtgttgttcc tgcctgaaag aaaatatatt caaaattgtt ttcatttgca aagttatttc     660
atgataataa ataaataaat aagctttcgc tggaaccaat taatattgca aaaggaattc     720
ttttattttt attttttta aattatactt taagttctag ggtacatgtg cacaacgtgc      780
```